US012747228B2

(12) United States Patent
Hatcher et al.

(10) Patent No.: US 12,747,228 B2
(45) Date of Patent: Sep. 29, 2026

(54) POTENT AND SELECTIVE INHIBITORS OF IRAK4

(71) Applicant: Dana-Farber Cancer Institute, Inc., Boston, MA (US)

(72) Inventors: John M. Hatcher, Boston, MA (US); Nathanael S. Gray, Jamaica Plain, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 319 days.

(21) Appl. No.: 18/690,160

(22) PCT Filed: Sep. 8, 2022

(86) PCT No.: PCT/US2022/042881

§ 371 (c)(1),
(2) Date: Mar. 7, 2024

(87) PCT Pub. No.: WO2023/039047

PCT Pub. Date: Mar. 16, 2023

(65) Prior Publication Data

US 2024/0391899 A1 Nov. 28, 2024

Related U.S. Application Data

(60) Provisional application No. 63/241,751, filed on Sep. 8, 2021.

(51) Int. Cl.

| | |
|---|---|
| ***C07D 401/14*** | (2006.01) |
| ***A61K 31/4545*** | (2006.01) |
| ***A61K 31/496*** | (2006.01) |
| ***A61K 45/06*** | (2006.01) |
| ***C07D 405/14*** | (2006.01) |
| ***C07D 413/14*** | (2006.01) |
| ***C07D 417/14*** | (2006.01) |

(52) U.S. Cl.
CPC ........ *C07D 401/14* (2013.01); *A61K 31/4545* (2013.01); *A61K 31/496* (2013.01); *A61K 45/06* (2013.01); *C07D 405/14* (2013.01); *C07D 413/14* (2013.01); *C07D 417/14* (2013.01)

(58) Field of Classification Search
CPC ................ C07D 231/02; C07D 401/14; A61K 31/4545; A61K 31/496
See application file for complete search history.

(56) References Cited

U.S. PATENT DOCUMENTS 10,040,798 B2 8/2018 Lim et al.

FOREIGN PATENT DOCUMENTS

| | | | | |
|---|---|---|---|---|
| WO | WO-2018081294 A1 * | 5/2018 | .............. A61P 43/00 |
| WO | WO-2019160915 A1 * | 8/2019 | ........... C07D 417/14 |
| WO | 2020150545 A1 | 7/2020 | |
| WO | WO 2021/127278 A1 | 6/2021 | |

OTHER PUBLICATIONS

Pubchem compound 7880461. Indexed on Oct. 19, 2014. (Year: 2014).*
Watson (Tetrahedron Letters vol. 38 pp. 9065-9068 published 1997) (Year: 1997).*
Huo (Molecules vol. 23 pp. 2116/1-2116/12 published 2018) (Year: 2018).*
Hatcher et al., "Discovery of a Selective, Covalent IRAK1 Inhibitor with Antiproliferative Activity in MYD88 Mutated B-Cell Lymphoma", *ACS Medicinal Chemistry Letters* 11(11):2238-2243 (2020).
International Search Report and Written Opinion for International Application No. PCT/US2022/042881 mailed Dec. 8, 2022, 7 pages.
PubChem CID 78830461, Create date: Oct. 19, 2014, 8 pages.
Extended European Search Report, EP Application No. 22868046.8, dated Jun. 17, 2025, 6 pages.

* cited by examiner

*Primary Examiner* — George W Kosturko
(74) *Attorney, Agent, or Firm* — Nielsen IP Law LLC

(57) ABSTRACT

The disclosure relates to compounds that act as inhibitors of interleukin 1 (IL-1) receptor-associated kinase 4 (IRAK4); pharmaceutical compositions comprising the compounds; and methods of treating or preventing kinase-mediated disorders, including cancer and other proliferation diseases.

18 Claims, No Drawings

POTENT AND SELECTIVE INHIBITORS OF IRAK4

CROSS-REFERENCE TO RELATED APPLICATIONS

This application claims the benefit of U.S. Provisional Patent Application No. 63/241,751, filed Sep. 8, 2021, the disclosure of which is incorporated herein by reference in its entirety.

BACKGROUND

Interleukin 1 (IL-1) receptor-associated kinases (IRAKs) are serine/threonine kinases that play critical roles in initiating innate immune responses against foreign pathogens. Altogether there are four IRAK kinases: IRAK1 and IRAK4, which are catalytically active kinases, and IRAK2 and IRAK3, which are believed to be catalytically inactive and are hence classified as “pseudokinases” (Flannery, S., et al. *Biochemical Pharmacology,* 2010, 80 (12), 1981-1991; Kawasaki, T., et al. *Front. Immunol.* 2014, 5, 8). IRAKs are downstream effectors of Toll-like receptor (TLR) and interleukin-1 receptor (IL-1R) pathways and play an important role in innate immune signaling. TLR stimulation leads to recruitment of MYD88, an adaptor molecule, to the activated receptor complex, which then complexes with IRAK4 and activates IRAK1. TRAF6 is then activated by IRAK1 leading to NFkB activation (Rhyasen, G. W., et al. *British Journal of Cancer* 2015, 112 (2), 232-237).

Dysregulated activation of the IRAK pathway in cancer cells further contributes to disease progression through inflammation of the tumor microenvironment. Waldenstrom’s Macroglobulinemia (WM) and a subset of activated B cell such as diffuse large B cell lymphomas (ABC DLBCLs) are characterized by oncogenic mutations in MYD88 that result in constitutive activation of the NFkB pathway (Ngo, V. N., et al. *Nature* 2011, 470 (7332), 115-119; Yang, G., et al. *Blood* 2013, 122 (7), 1222-1232). TLRs and their associated signal transducers are frequently overexpressed and/or constitutively activated in myelodysplastic syndromes (MDS). Finally, the overexpression of the oncogenic long form of IRAK4 (IRAK4-L) has been found in over half of cases of AML and MDS and portends worse prognosis (Smith, M., et al. *Nature Cell Biology* 2019, 21 (5), 640-650; Choudhary, G. S., et al. *Blood* 2019, 134 (Supp. 1), 4224). Thus, IRAKs are attractive therapeutic targets for the treatment of MDS, AML, and other tumors with altered innate immune signaling.

IRAK4 kinase-inactive mice have also been shown to be resistant to the development of Alzheimer’s disease, a process that is thought to be due to reduced IL-1 production and signaling (Cameron, B., et al. *Journal of Neuroscience* 2012, 32 (43), 15112-15123). Similarly, small molecule inhibitors of IRAK4 have been reported to inhibit TLR induced inflammatory signaling in vitro and in vivo (Tumey, L. N., et al., *Bioorg. Med. Chem. Lett.* 2014, 24 (9), 2066-2072; Kelly, P. N., et al. *Journal of Experimental Medicine* 2015, 212 (13), 2189-2201). In addition, in vivo administration of IRAK4 inhibitors has been observed to reduce gout-like inflammation in the uric acid induced peritonitis model, ischemia induced inflammation in 5/6 nephrectomized rats, and mouse models of lupus (Dudhgaonkar, S., et al. *Journal of Immunology* 2017, 198 (3), 1308-1319).

IRAK4 has therefore been recognized as an important pharmacological target for the treatment of chronic inflammatory diseases. Accordingly, there is a need for potent and selective inhibitors of IRAK4.

SUMMARY

The present disclosure provides, inter alia, a compound of Formula (I):

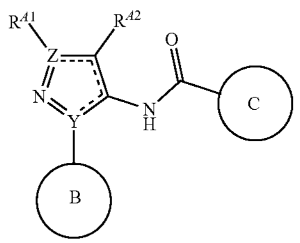

(I)

or a pharmaceutically acceptable salt thereof, wherein:

$R^{A1}$ is $C_{3-10}$ cycloalkyl or 4- to 10-membered heterocyclyl, wherein the cycloalkyl and heterocyclyl are unsubstituted or substituted with one, two, or three $R^1$;

$R^{A2}$ is H;

or $R^{A1}$ and $R^{A2}$ taken together with the atoms to which they are bound form a $C_{3-10}$ cycloalkyl or a 5- to 10-membered heterocyclyl, wherein the cycloalkyl and heterocyclyl are unsubstituted or substituted with one, two, or three $R^{11}$;

B is $C_{6-10}$ aryl or 5- to 10-membered heteroaryl, wherein the aryl and heteroaryl are unsubstituted or substituted with one, two, or three $R^2$;

C is pyridinyl that is unsubstituted or substituted with one, two, or three $R^3$;

$R^1$ and $R^{11}$, independently for each occurrence, are $C_{1-8}$ alkyl, $C_{1-8}$ haloalkyl, $C_{1-8}$ alkoxy, halo, $C_{3-8}$ cycloalkyl, or 3- to 8-membered heterocyclyl;

$R^2$, independently for each occurrence, is $C_{1-6}$ alkyl, $C_{3-6}$ cycloalkyl, $C_{1-6}$ haloalkyl, $C_{1-6}$ alkoxy, halo, or —CN;

$R^3$, independently for each occurrence, is —OH, —CN, halo, —C(X)OR$^5$, —C(X)N(R$^5$)(R$^6$), $C_{1-8}$ alkyl, $C_{2-8}$ alkenyl, $C_{1-8}$ haloalkyl, $C_{1-8}$ alkoxy, $C_{3-10}$ cycloalkyl, 4- to 10-membered heterocyclyl, $C_{6-10}$ aryl, 5- to 10-membered heteroaryl, $C_{1-3}$ alkyl-(4- to 10-membered heterocyclyl), $C_{1-3}$ alkyl-(5- to 10-membered heteroaryl), —O—$C_{1-3}$ alkyl-(4- to 10-membered heterocyclyl), or —O—$C_{1-3}$ alkyl-(5- to 10-membered heteroaryl) wherein the alkyl, alkenyl, haloalkyl, alkoxy, cycloalkyl, heterocyclyl, aryl, heteroaryl, alkylheterocyclyl, alkylheteroaryl, —O-alkylheterocyclyl, and —O-alkylheteroaryl are unsubstituted or substituted with one, two, or three $R^4$;

$R^4$, independently for each occurrence, is oxo, —OH, —CN, halo, $C_{1-4}$ alkyl, $C_{1-4}$ haloalkyl, $C_{1-4}$ alkoxy, —$C_{0-3}$ alkyl-C(X)OR$^5$, —$C_{0-3}$ alkyl-C(X)N(R$^5$)(R$^6$), or —$C_{0-3}$ alkyl-(5- to 10-membered heteroaryl), wherein the alkylheteroaryl is unsubstituted or substituted with one, two, or three $C_{1-3}$ alkyl or halo;

X is, independently for each occurrence, O or S;

Y is C or N;

Z is C or N; and $R^5$ and $R^6$ are each, independently, hydrogen or $C_{1-4}$ alkyl;

provided that when Y is C, then Z is N, and when Y is N, then Z is C; and provided that when B is unsubstituted, either $R^1$ is not isopropyl or $R^3$ is not

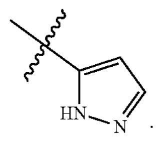 [SMILES: *c1ccn[nH]1]

In some embodiments, the compound has a structure according to Formula (I-a), (I-b), or (I-c):

(I-a)

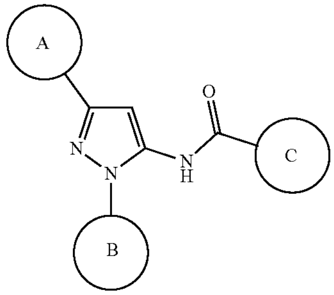

(I-b)

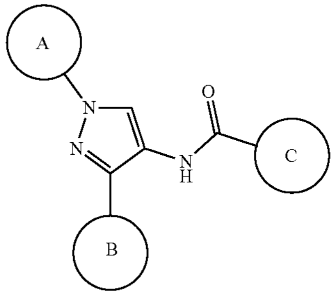

(I-c)

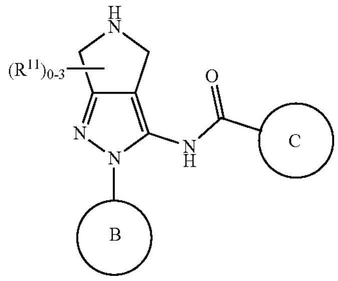

wherein A is $C_{3-10}$ cycloalkyl or 4- to 10-membered heterocycyl, wherein the cycloalkyl and heterocycyl are unsubstituted or substituted with one, two, or three $R^1$.

In some embodiments, the compound has a structure according to Formula (I-a):

(I-a)

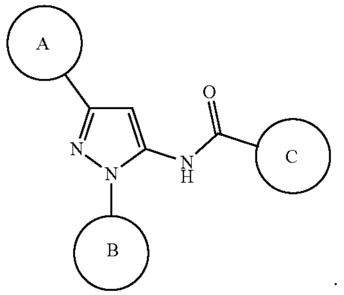

n some embodiments, A is a 4- to 6-membered heterocyclyl having 1 or 2 nitrogen atoms and 0 or 1 oxygen atoms, wherein the heterocyclyl is unsubstituted or substituted with one, two, or three $R^1$. In some embodiments, A is piperidinyl that is unsubstituted or substituted with one, two, or three $R^1$. In some embodiments, $R^1$, independently for each occurrence, is $C_{1-4}$ alkyl, $C_{1-4}$ haloalkyl, $C_{1-4}$ alkoxy, halo, $C_{3-6}$ cycloalkyl, or 3- to 6-membered heterocyclyl.

In some embodiments, the compound has a structure according to Formula (I-a1):

(I-a1)

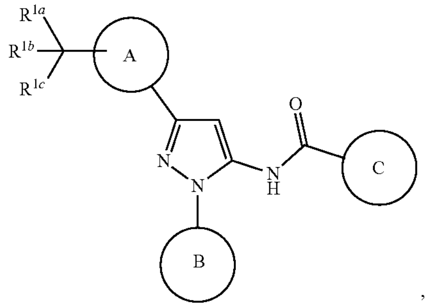

wherein:

$R^{1a}$ is H or $CH_3$;

$R^{1b}$ is H or $C_{1-3}$ alkyl;

$R^{1c}$ is H or $C_{1-3}$ alkyl; or $R^{1a}$ is H and $R^{1b}$ and $R^{1c}$ taken together form a $C_{3-4}$ cycloalkyl or a 3- to 4-membered heterocyclyl along with the carbon atom to which they are attached.

In some embodiments, the compound has a structure according to Formula (I-a2):

(I-a2)

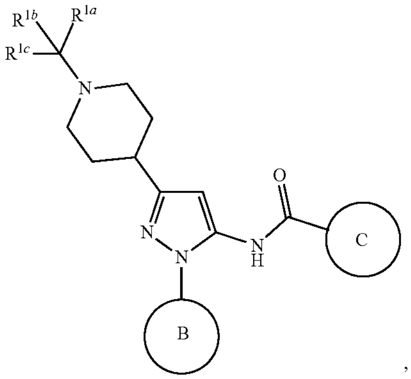

, wherein $R^{1a}$, $R^{1b}$, and $R^{1c}$ are as defined above.

In some embodiments, A is selected from the group consisting of:

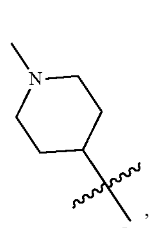

,

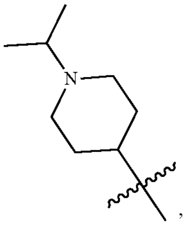

, and

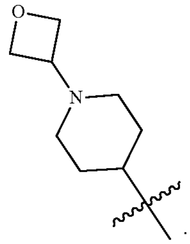

.

In some embodiments, B is pyridinyl that is unsubstituted or substituted with one, two, or three $R^2$. In some embodiments, B is unsubstituted or substituted with one $R^2$. In some embodiments, $R^2$ independently for each occurrence is $C_{1-4}$ alkyl, cyclopropyl, cyclobutyl, —$CF_3$, —$CHF_2$, —$CH_2F$, $C_{1-4}$ alkoxy, halo, or —CN. In some embodiments, B is unsubstituted or substituted with methyl.

In some embodiments, the compound has a structure according to Formula (I-a3):

(I-a3)

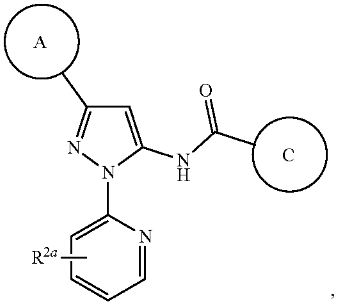

, wherein $R^{2a}$ is H, $C_{1-4}$ alkyl, cyclopropyl, cyclobutyl, —$CF_3$, —$CHF_2$, —$CH_2F$, $C_{1-4}$ alkoxy, halo, or —CN.

In some embodiments, the compound has a structure according to Formula (I-a4):

(I-a4)

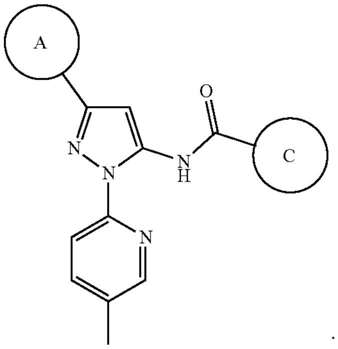

.

In some embodiments, the compound has a structure according to Formula (I-a5):

(1-a5)

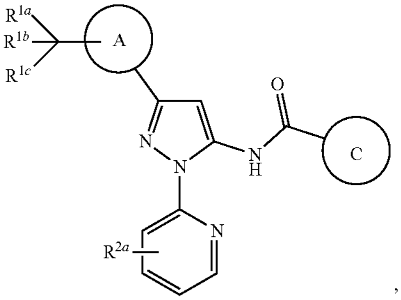

, wherein $R^{1a}$, $R^{1b}$, and $R^{1c}$ are as defined above, and wherein $R^{2a}$ is H, $C_{1-4}$ alkyl, cyclopropyl, cyclobutyl, —$CF_3$, —$CHF_2$, —$CH_2F$, $C_{1-4}$ alkoxy, halo, or —CN.

In some embodiments, $R^3$, independently for each occurrence, is —$C(X)N(R^5)(R^6)$, $C_{1-8}$ alkyl, $C_{2-8}$ alkenyl, $C_{3-10}$ cycloalkyl, 4- to 10-membered heterocyclyl, $C_{6-10}$ aryl, 5- to 10-membered heteroaryl, or $C_{1-3}$ alkyl-(5- to 10-membered heteroaryl) wherein the alkyl, alkenyl, cycloalkyl, heterocyclyl, aryl, heteroalkyl, and alkylheteroaryl are unsubstituted or substituted with one, two, or three $R^4$.

In some embodiments, $R^4$ is oxo, halo, $C_{1-4}$ alkyl, —$C_{0-3}$ alkyl-$C(X)N(R^5)(R^6)$, or —$C_{0-3}$ alkyl-(5- to 10-membered heteroaryl), wherein the alkylheteroaryl is unsubstituted or substituted with one, two, or three $C_{1-3}$ alkyl or halo; X is O; and $R^5$ and $R^6$ are each, independently, hydrogen or methyl.

In some embodiments, the compound has an inhibitory activity of IRAK4 that is at least about ten times greater than its inhibitory activity of IRAK1.

In some embodiments, the compound is selected from the group consisting of compound 001 to compound 021.

The present disclosure also provides a pharmaceutical composition comprising a compound disclosed herein and a pharmaceutically acceptable carrier.

The present disclosure further provides a method of inhibiting interleukin-1 receptor-associated kinase 4 (IRAK4) in a subject in need thereof, the method comprising administering to the subject a therapeutically effective amount of a compound or a pharmaceutical composition disclosed herein. The present disclosure still further provides a method of treating a proliferative disease or disorder in a subject in need thereof comprising administering to the subject a therapeutically effective amount of a compound or a pharmaceutical composition disclosed herein.

The present disclosure also provides a method of treating an inflammatory disease or disorder in a subject in need thereof comprising administering to the subject a therapeutically effective amount of a compound or a pharmaceutical composition disclosed herein. In some embodiments, the inflammatory disease or disorder is selected from the group consisting of myocardial dysfunction, autoimmune conditions associated with hyperinflammation, and septic response. In some embodiments, the inflammatory disease or disorder is myocardial contractile dysfunction following burn or sepsis-induced myocardial dysfunction. In some embodiments, the inflammatory disease or disorder is microbial septic response.

The present disclosure also provides a method of treating cancer in a subject in need thereof comprising administering to the subject a therapeutically effective amount of a compound or a pharmaceutical composition disclosed herein. In some embodiments, the cancer is selected from the group consisting of human myelodysplastic syndrome (MDS), leukemia, breast cancer, and lymphoma. In some embodiments, the cancer is triple-negative breast cancer. In some embodiments, the cancer is acute myeloid leukemia (AML). In some embodiments, the cancer is an activated B cell lymphoma. In some embodiments, the cancer is diffuse large B cell lymphoma. In some embodiments, the cancer is Waldenström macroglobulinemia.

In some embodiments, any of the methods further comprises administering a second pharmaceutical agent. In some embodiments, the second pharmaceutical agent is a kinase inhibitor. In some embodiments, the second pharmaceutical agent is a Bruton's tyrosine kinase (BTK) inhibitor.

DETAILED DESCRIPTION

Definitions

Listed below are definitions of various terms used to describe the compounds and compositions disclosed herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "administration" or the like as used herein refers to the providing a therapeutic agent to a subject. Multiple techniques of administering a therapeutic agent exist in the art including, but not limited to, intravenous, oral, aerosol, parenteral, ophthalmic, pulmonary, and topical administration.

The term "treat," "treated," "treating," or "treatment" includes the diminishment or alleviation of at least one symptom associated or caused by the state, disorder or disease being treated. In certain embodiments, the treatment comprises bringing into contact with IRAK4 an effective amount of a compound disclosed herein for conditions related to cancer.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the present disclosure, and are physiologically acceptable to the patient. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

An "oral dosage form" includes a unit dosage form prescribed or intended for oral administration. In an embodiment of the pharmaceutical combinations provided herein, the IRAK4 inhibitors disclosed herein is administered as an oral dosage form.

As used herein, the term "IRAK" refers to interleukin 1 (IL-1) receptor-associated kinases and may refer to the wild-type receptor or to a receptor containing one or more mutations.

As used herein, the term "alkyl," by itself or as part of another substituent means, unless otherwise stated, a straight or branched chain hydrocarbon having the number of carbon atoms designated (i.e., $C_1$-$C_6$ alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_1$-$C_6$ alkyl include ethyl, methyl, isopropyl, isobutyl, n-pentyl, and n-hexyl.

As used herein, the term "alkoxy" refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "alkenyl" refers to a monovalent group derived from a hydrocarbon moiety containing, in certain embodiments, from two to six, or two to eight carbon atoms having at least one carbon-carbon double bond. The alkenyl group may or may not be the point of attachment to another group. The term "alkenyl" includes, but is not limited to, ethenyl, 1-propenyl, 1-butenyl, heptenyl, octenyl and the like.

As used herein,

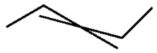

represents a double bond that may be in either the E or Z configuration. Accordingly, the group

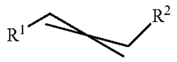

may be

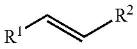

or

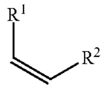

or a mixture thereof.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is fully or partially saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term "heterocyclyl" or "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. Accordingly, The term "heterocyclyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2-pyrrolidinonyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo [2.1.1]hexanyl, 5-azabicyclo[2.1.1]hexanyl, 6-azabicyclo [3.1.1] heptanyl, 2-azabicyclo[2.2.1]heptanyl, 3-aza-bicyclo [3.1.1]heptanyl, 2-azabicyclo[3.1.1]heptanyl, 3-azabicyclo [3.1.0]hexanyl, 2-azabicyclo-[3.1.0]hexanyl, 3-azabicyclo [3.2.1]octanyl, 8-azabicyclo[3.2.1]octanyl, 3-oxa-7-azabicyclo[3.3.1]-nonanyl, 3-oxa-9-azabicyclo[3.3.1] nonanyl, 2-oxa-5-azabicyclo[2.2.1]heptanyl, 6-oxa-3-aza-bicyclo[3.1.1]heptanyl, 2-azaspiro[3.3]heptanyl, 2-oxa-6-azaspiro[3.3]heptanyl, 2-oxaspiro[3.3]-heptanyl, 2-oxaspiro [3.5]nonanyl, 3-oxaspiro[5.3]nonanyl, 2-azaspiro[3.3] heptane, 8-oxabicyclo[3.2.1]octanyl, 2,8-diazaspiro[4.5] decan-1-onyl, and 1,8-diazaspiro[4.5]decan-2-onyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclo-penta[c]pyridinyl, 1,4,5,6-tetrahydrocyclopenta[c]pyrazolyl, 2,4,5,6-tetrahydrocyclopenta[c]-pyrazolyl, 5,6-dihydro-4H-pyrrolo [1,2-b]pyrazolyl, 6,7-dihydro-5H-pyrrolo[1,2-b][1,2,4] triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thienyl, and so forth.

As used herein, the term "substituted" means that an atom or group of atoms has replaced hydrogen as the substituent attached to another group.

Compounds

Provided herein are compounds that are inhibitors of interleukin 1 receptor-associated kinase 4 (IRAK4) useful in the treatment of kinase-mediated disorders, including cancer and other proliferation diseases.

In an aspect, provided herein is a compound of Formula (I):

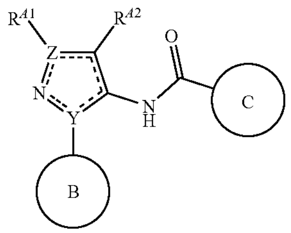

(I)

or a pharmaceutically acceptable salt thereof, wherein:

$R^{A1}$ is $C_{3-10}$ cycloalkyl or 4- to 10-membered heterocyclyl, wherein the cycloalkyl and heterocyclyl are unsubstituted or substituted with one, two, or three $R^1$;

$R^{A2}$ is H;

or $R^{A1}$ and $R^{A2}$ taken together with the atoms to which they are bound form a $C_{3-10}$ cycloalkyl or a 5- to 10-membered heterocyclyl, wherein the cycloalkyl and heterocyclyl are unsubstituted or substituted with one, two, or three $R^{11}$;

B is $C_{6-10}$ aryl or 5- to 10-membered heteroaryl, wherein the aryl and heteroaryl are unsubstituted or substituted with one, two, or three $R^2$;

C is pyridinyl that is unsubstituted or substituted with one, two, or three $R^3$;

$R^1$ and $R^{11}$, independently for each occurrence, are $C_{1-8}$ alkyl, $C_{1-8}$ haloalkyl, $C_{1-8}$ alkoxy, halo, $C_{3-8}$ cycloalkyl, or 3- to 8-membered heterocyclyl;

$R^2$, independently for each occurrence, is $C_{1-6}$ alkyl, $C_{3-6}$ cycloalkyl, $C_{1-6}$ haloalkyl, $C_{1-6}$ alkoxy, halo, or —CN;

$R^3$, independently for each occurrence, is —OH, —CN, halo, —C(X)OR$^5$, —C(X)N(R$^5$)(R$^6$), $C_{1-8}$ alkyl, $C_{2-8}$ alkenyl, $C_{1-8}$ haloalkyl, $C_{1-8}$ alkoxy, $C_{3-10}$ cycloalkyl, 4- to 10-membered heterocyclyl, $C_{6-10}$ aryl, 5- to 10-membered heteroaryl, $C_{1-3}$ alkyl-(4- to 10-membered heterocyclyl), $C_{1-3}$ alkyl-(5- to 10-membered heteroaryl), —O—$C_{1-3}$ alkyl-(4- to 10-membered heterocyclyl), or —O—$C_{1-3}$ alkyl-(5- to 10-membered heteroaryl) wherein the alkyl, alkenyl, cycloalkyl, heterocyclyl, aryl, heteroaryl, alkylheterocyclyl, alkylheteroaryl, —O-alkylheterocyclyl, and —O-alkylheteroaryl are unsubstituted or substituted with one, two, or three $R^4$;

$R^4$, independently for each occurrence, is oxo, —OH, —CN, halo, $C_{1-4}$ alkyl, $C_{1-4}$ haloalkyl, $C_{1-4}$ alkoxy, —$C_{0-3}$ alkyl-C(X)OR$^5$, —$C_{0-3}$ alkyl-C(X)N(R$^5$)(R$^6$), or —$C_{0-3}$ alkyl-(5- to 10-membered heteroaryl), wherein the alkylheteroaryl is unsubstituted or substituted with one, two, or three $C_{1-3}$ alkyl or halo;

X is, independently for each occurrence, O or S;

Y is C or N;

Z is C or N; and $R^5$ and $R^6$ are each, independently, hydrogen or $C_{1-4}$ alkyl;

provided that when Y is C, then Z is N, and when Y is N, then Z is C; and provided that when B is unsubstituted either $R^1$ is not isopropyl or $R^3$ is not

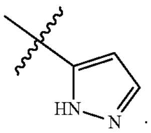 [SMILES: *c1ccn[nH]1]

.

In an embodiment, when B is unsubstituted, either $R^1$ is methyl or $R^3$ is not

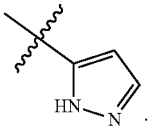 [SMILES: *c1ccn[nH]1]

.

In another embodiment, when B is unsubstituted, $R^3$ is not

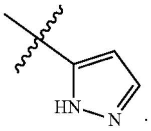 [SMILES: *c1ccn[nH]1]

.

In a yet another embodiment, $R^3$ is not:

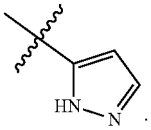 [SMILES: *c1ccn[nH]1]

.

In an embodiment, $R^{A1}$ is $C_{3-10}$ cycloalkyl or 4- to 10-membered heterocyclyl, wherein the cycloalkyl and heterocyclyl are unsubstituted or substituted with one, two, or three $R^1$, and $R^{A2}$ is H. In another embodiment, $R^{A1}$ is $C_{4-6}$ cycloalkyl or 4- to 6-membered heterocyclyl, wherein the cycloalkyl or heterocyclyl are unsubstituted or substituted with one, two, or three $R^1$, and $R^{A2}$ is H. In yet another embodiment, $R^{A1}$ is a 4- to 6-membered heterocyclyl that is unsubstituted or substituted with one, two, or three $R^1$, and $R^{A2}$ is H.

In an embodiment, $R^{A1}$ is 4- to 6-membered heterocyclyl having 1 or 2 nitrogen atoms and 0 or 1 oxygen atoms, wherein the heterocyclyl is unsubstituted or substituted with one, two, or three $R^1$, and $R^{A2}$ is H. In another embodiment, $R^{A1}$ is azetidinyl, 1,3-diazetidinyl, pyrrolidinyl, pyrazolidinyl, imidazolidinyl, piperidinyl, piperazinyl, or morpholinyl, each of which is unsubstituted or substituted with one, two, or three $R^1$, and $R^{A2}$ is H. In yet another embodiment, $R^{A1}$ is azetidinyl, imidazolidinyl, piperidinyl, piperazinyl, or morpholinyl, each of which is unsubstituted or substituted with one, two, or three $R^1$, and $R^{A2}$ is H. In still another embodiment, $R^{A1}$ is azetidinyl, imidazolidinyl, piperidinyl, piperazinyl, or morpholinyl, each of which is unsubstituted or substituted with one or two $R^1$, and $R^{A2}$ is H. In an embodiment, $R^{A1}$ is piperidinyl that is unsubstituted or substituted with one, two, or three $R^1$, and $R^{A2}$ is H. In another embodiment, $R^{A1}$ is piperidinyl that is unsubstituted or substituted with one $R^1$, and $R^{A2}$ is H In an embodiment, $R^{A1}$ and $R^{A2}$ taken together with the atoms to which they are bound form a $C_{3-10}$ cycloalkyl or a 5- to 10-membered heterocyclyl, wherein the cycloalkyl and heterocyclyl are unsubstituted or substituted with one, two, or three $R^{11}$. In another embodiment, $R^{A1}$ and $R^{A2}$ taken together with the atoms to which they are bound form a 5- to 10-membered heterocyclyl that is unsubstituted or substituted with one, two, or three $R^{11}$. In yet another embodiment, $R^{A1}$ and $R^{A2}$ taken together with the atoms to which they are bound form a 5- to 10-membered heterocyclyl having 1 or 2 nitrogen atoms, wherein the heterocyclyl is unsubstituted or substituted with one, two, or three $R^{11}$. In yet another embodiment, $R^{A1}$ and $R^{A2}$ taken together with the atoms to which they are bound form a 5-membered heterocyclyl having 1 or 2 nitrogen atoms, wherein the heterocyclyl is unsubstituted or substituted with one, two, or three $R^{11}$.

In an embodiment, $R^1$ independently for each occurrence is $C_{1-4}$ alkyl, $C_{1-4}$ haloalkyl, $C_{1-4}$ alkoxy, halo, $C_{3-6}$ cycloalkyl, or 3- to 6-membered heterocyclyl. In another embodiment, $R^1$ independently for each occurrence is $C_{1-4}$ alkyl, halo, $C_{3-6}$ cycloalkyl, or 3- to 6-membered heterocyclyl. In yet another embodiment, $R^1$ is methyl, ethyl, propyl, isopropyl, butyl, sec-butyl, tert-butyl, cyclopropyl, cyclobutyl, oxetanyl, azetidinyl, or fluoro.

In an embodiment, $R^1$ independently for each occurrence is $C_{1-8}$ alkyl, halo, $C_{3-8}$ cycloalkyl, or 3- to 8-membered heterocyclyl. In another embodiment, $R^1$ independently for each occurrence is $C_{1-8}$ alkyl, $C_{3-8}$ cycloalkyl, or 3- to 8-membered heterocyclyl. In yet another embodiment, $R^1$ independently for each occurrence is $C_{1-4}$ alkyl, $C_{3-6}$ cycloalkyl, or 3- to 6-membered heterocyclyl.

In an embodiment, B is phenyl or 5- to 6-membered heteroaryl, wherein the phenyl and heteroaryl are unsubstituted or substituted with one, two, or three $R^2$. In another embodiment, B is phenyl or 5- to 6-membered heteroaryl having 1 or 2 nitrogen atoms, wherein the phenyl and heteroaryl are unsubstituted or substituted with one, two, or three $R^2$. In another embodiment, B is phenyl, pyridinyl, pyrimidinyl, pyridazinyl, or pyrazinyl, each of which are unsubstituted or substituted with one, two, or three $R^2$. In yet another embodiment, B is pyridinyl that is unsubstituted or substituted with one, two, or three $R^2$. In still another embodiment, B is methylpyridinyl.

In an embodiment, B is unsubstituted or substituted with $C_{1-6}$ alkyl. In another embodiment, B is unsubstituted or substituted with methyl.

In an embodiment, B is substituted with one $R^2$.

In an embodiment, B is:

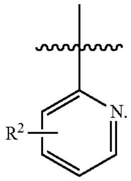

.

In another embodiment, B is:

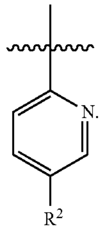

In yet another embodiment, B is:

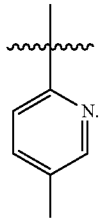 [SMILES: *c1ccc(C)cn1]

In an embodiment, $R^2$ independently for each occurrence is $C_{1-4}$ alkyl, cyclopropyl, cyclobutyl, $C_{1-4}$ haloalkyl, $C_{1-4}$ alkoxy, halo, or —CN. In another embodiment, $R^2$ independently for each occurrence is $C_{1-4}$ alkyl, cyclopropyl, cyclobutyl, —$CF_3$, —$CHF_2$, —$CH_2F$, $C_{1-4}$ alkoxy, halo, or —CN.

In an embodiment, $R^2$ independently for each occurrence is $C_{1-6}$ alkyl. In another embodiment, $R^2$ independently for each occurrence is $C_{1-4}$ alkyl. In yet another embodiment, $R^2$ independently for each occurrence is methyl.

In an embodiment, B is:

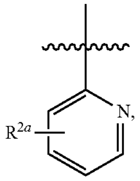

wherein $R^{2a}$ is H, $C_{1-6}$ alkyl, $C_{3-6}$ cycloalkyl, $C_{1-6}$ haloalkyl, $C_{1-6}$ alkoxy, halo, or —CN.

In another embodiment, B is:

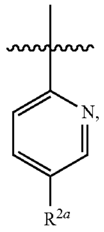

wherein $R^{2a}$ is H, $C_{1-6}$ alkyl, $C_{3-6}$ cycloalkyl, $C_{1-6}$ haloalkyl, $C_{1-6}$ alkoxy, halo, or —CN.

In an embodiment, $R^{2a}$ is H, $C_{1-4}$ alkyl, cyclopropyl, cyclobutyl, $C_{1-4}$ haloalkyl, $C_{1-4}$ alkoxy, halo, or —CN. In another embodiment, $R^{2a}$ is H, $C_{1-4}$ alkyl, cyclopropyl, cyclobutyl, —$CF_3$, —$CHF_2$, —$CH_2F$, $C_{1-4}$ alkoxy, halo, or —CN. In yet another embodiment, $R^{2a}$ is H or $C_{1-6}$ alkyl. In still another embodiment, $R^{2a}$ is H or $C_{1-4}$ alkyl. In an embodiment, $R^{2a}$ is H or methyl. In an embodiment, $R^{2a}$ is methyl.

In an embodiment, C is pyridinyl that is substituted with one, two, or three $R^3$. In another embodiment, C is pyridinyl that is substituted with one $R^3$.

In an embodiment, $R^3$ independently for each occurrence, is —C(X)N($R^5$)($R^6$), $C_{1-8}$ alkyl, $C_{2-8}$ alkenyl, $C_{3-10}$ cycloalkyl, 4- to 10-membered heterocyclyl, $C_{6-10}$ aryl, 5- to 10-membered heteroaryl, $C_{1-3}$ alkyl-(4- to 10-membered heterocyclyl), $C_{1-3}$ alkyl-(5- to 10-membered heteroaryl), —O—$C_{1-3}$ alkyl-(4- to 10-membered heterocyclyl), or —O—$C_{1-3}$ alkyl-(5- to 10-membered heteroaryl) wherein the alkyl, alkenyl, cycloalkyl, heterocyclyl, aryl, heteroaryl, alkylheterocyclyl, alkylheteroaryl, —O-alkylheterocyclyl, and —O-alkylheteroaryl are unsubstituted or substituted with one, two, or three $R^4$.

In another embodiment, $R^3$ independently for each occurrence is —OH, —CN, halo, —C(X)O$R^5$, —C(X)N($R^5$)($R^6$), $C_{1-8}$ alkyl, $C_{2-8}$ alkenyl, $C_{1-8}$ haloalkyl, $C_{1-8}$ alkoxy, $C_{3-10}$ cycloalkyl, 4- to 10-membered heterocyclyl, $C_{6-10}$ aryl, 5- to 10-membered heteroaryl, or $C_{1-3}$ alkyl-(5- to 10-membered heteroaryl) wherein the alkyl, alkenyl, haloalkyl, alkoxy, cycloalkyl, heterocyclyl, aryl, heteroaryl, and alkylheteroaryl are unsubstituted or substituted with one, two, or three $R^4$.

In an embodiment, C is represented by a formula selected from the group consisting of (II-a) to (II-l):

(II-a)

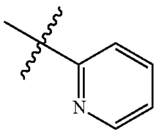, (II-b)

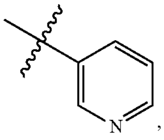, (II-c)

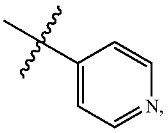

(II-d)

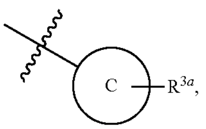

(II-e)

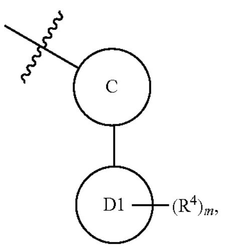

-continued (II-f)

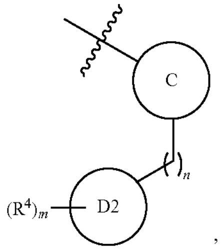

, (II-g)

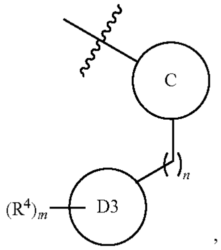

, (II-h)

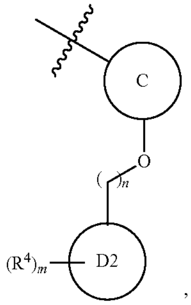

, (II-i)

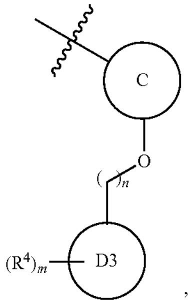

, (II-j)

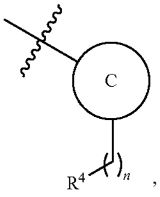

, (II-k)

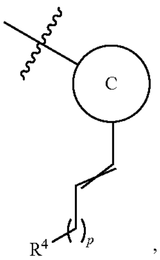

, or

-continued (II-l)

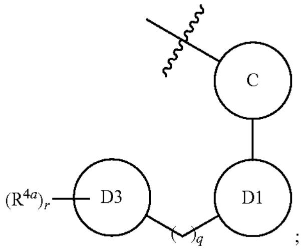

;

wherein:

$R^{3a}$ is —OH, —CN, halo, $C_{1-4}$ alkyl, $C_{1-4}$ haloalkyl, or $C_{1-4}$ alkoxy;

$R^{4a}$ is $C_{1-3}$ alkyl or halo;

D1 is $C_{3-10}$ cycloalkyl, 4- to 10-membered heterocyclyl, $C_{6-10}$ aryl, or 5- to 10-membered heteroaryl;

D2 is 4- to 10-membered heterocyclyl;

D3 is 5- to 10-membered heteroaryl;

m, p, q, and r are independently 0, 1, 2, or 3; and n is 1, 2, 3, or 4.

In some embodiments, C is represented by a formula selected from the group consisting of (II-a) to (II-c) or (II-d') to (II-l'):

(II-a)

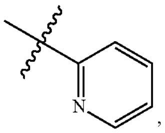

(II-b)

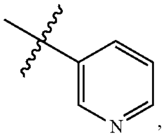

(II-c)

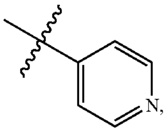

(II-d')

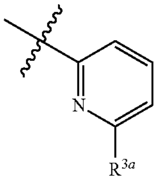

(II-e')

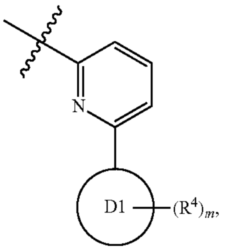

-continued (II-f')

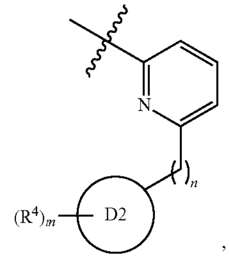

, (II-g')

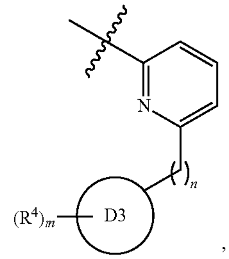

, (II-h')

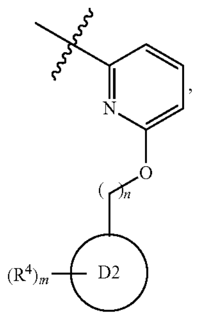

(II-i')

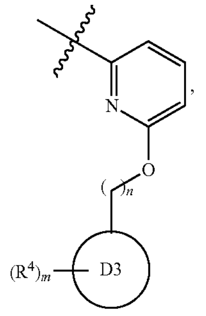

(II-j')

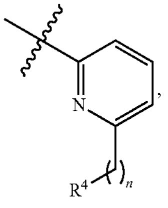

-continued (II-k')

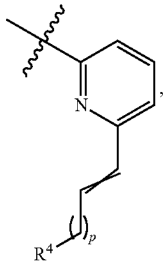

or (II-l')

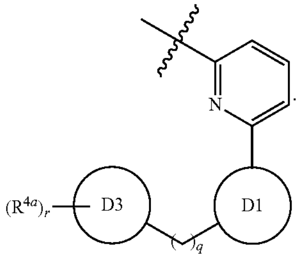

In an embodiment, $R^{3a}$ is —CN or $C_{1-4}$ alkyl.

In an embodiment, D1 is 4- to 10-membered heterocyclyl or 5- to 10-membered heteroaryl. In another embodiment, D1 is 4- to 10-membered heterocyclyl, phenyl, or 5- to 6-membered heteroaryl. In yet another embodiment, D1 is tetrahydrofuryl, pyrrolidinyl, pyrrolidinonyl, tetrahydrothiophenyl, tetrahydropyranyl, tetrahydrothiopyranyl, piperidinyl, morpholinyl, piperazinyl, diazaspirodecanonyl, phenyl, pyrrolyl, furanyl, thiophenyl, pyrazolyl, imadazolyl, triazolyl, oxazolyl, isoxazolyl, thiazolyl, isothiazolyl, oxadiazolyl, pyridinyl, pyridazinyl, pyrimidinyl, or pyrazinyl. In still another embodiment, D1 is pyrrolidinyl, pyrrolidinonyl, piperidinyl, morpholinyl, piperazinyl, diazaspirodecanonyl, pyrazolyl, imadazolyl, triazolyl, oxazolyl, isoxazolyl, thiazolyl, isothiazolyl, or oxadiazolyl.

In an embodiment, D2 is 4- to 6-membered heterocyclyl. In another embodiment, D2 is tetrahydrofuryl, pyrrolidinyl, pyrrolidinonyl, tetrahydrothiophenyl, tetrahydropyranyl, tetrahydrothiopyranyl, piperidinyl, morpholinyl, piperazinyl, or diazaspirodecanonyl. In yet another embodiment, D2 is pyrrolidinyl, pyrrolidinonyl, piperidinyl, morpholinyl, piperazinyl, or diazaspirodecanonyl.

In an embodiment, D3 is 5- to 6-membered heteroaryl. In another embodiment, D3 is pyrrolyl, furanyl, thiophenyl, pyrazolyl, imadazolyl, triazolyl, oxazolyl, isoxazolyl, thiazolyl, isothiazolyl, oxadiazolyl, pyridinyl, pyridazinyl, pyrimidinyl, or pyrazinyl. In yet another embodiment, D3 is pyrazolyl, imadazolyl, triazolyl, oxazolyl, isoxazolyl, thiazolyl, isothiazolyl, or oxadiazolyl.

In an embodiment, D1 is 4- to 10-membered heterocyclyl, phenyl, or 5- to 6-membered heteroaryl; D2 is 4- to 10-membered heterocyclyl; and D3 is 5- to 6-membered heteroaryl. In another embodiment, D1 is tetrahydrofuryl, pyrrolidinyl, pyrrolidinonyl, tetrahydrothiophenyl, tetrahydropyranyl, tetrahydrothiopyranyl, piperidinyl, morpholinyl, piperazinyl, diazaspirodecanonyl, phenyl, pyrrolyl, furanyl, thiophenyl, pyrazolyl, imadazolyl, triazolyl, oxazolyl, isoxazolyl, thiazolyl, isothiazolyl, oxadiazolyl, pyridinyl, pyridazinyl, pyrimidinyl, or pyrazinyl; D2 is tetrahydrofuryl, pyrrolidinyl, pyrrolidinonyl, tetrahydrothiophenyl, tetrahydropyranyl, tetrahydrothiopyranyl, piperidinyl, morpholinyl, piperazinyl, or diazaspirodecanonyl; and D3 is pyrrolyl, furanyl, thiophenyl, pyrazolyl, imadazolyl, triazolyl, oxazolyl, isoxazolyl, thiazolyl, isothiazolyl, oxadiazolyl, pyridinyl, pyridazinyl, pyrimidinyl, or pyrazinyl. In yet another embodiment, D1 is pyrrolidinyl, pyrrolidinonyl, piperidinyl, morpholinyl, piperazinyl, diazaspirodecanonyl, pyrazolyl, imadazolyl, triazolyl, oxazolyl, isoxazolyl, thiazolyl, isothiazolyl, or oxadiazolyl; D2 is pyrrolidinyl, pyrrolidinonyl, piperidinyl, morpholinyl, piperazinyl, or diazaspirodecanonyl; and D3 is pyrazolyl, imadazolyl, triazolyl, oxazolyl, isoxazolyl, thiazolyl, isothiazolyl, or oxadiazolyl.

In an embodiment, m is 0, 1, or 2. In another embodiment, n is 1 or 2. In another embodiment, p is 0. In yet another embodiment, q is 1. In still another embodiment, r is 0.

In an embodiment, $R^4$ independently for each occurrence is oxo, halo, $C_{1-4}$ alkyl, —$C_{0-3}$ alkyl-C(X)N($R^5$)($R^6$), or —$C_{0-3}$ alkyl-(5- to 10-membered heteroaryl), wherein the alkylheteroaryl is unsubstituted or substituted with one, two, or three $C_{1-3}$ alkyl or halo. In another embodiment, $R^4$ independently for each occurrence is oxo, halo, $C_{1-4}$ alkyl, —C(X)N($R^5$)($R^6$), or —$C_{0-3}$ alkyl-(5- to 6-membered heteroaryl).

In an embodiment, X is O. In another embodiment, X is S.

In an embodiment, $R^5$ and $R^6$ are each, independently, hydrogen or methyl.

In an embodiment, $R^4$ independently for each occurrence is oxo, halo, $C_{1-4}$ alkyl, —$C_{0-3}$ alkyl-C(X)N($R^5$)($R^6$), or —$C_{0-3}$ alkyl-(5- to 10-membered heteroaryl), wherein the alkylheteroaryl is unsubstituted or substituted with one, two, or three $C_{1-3}$ alkyl or halo; X is O; and $R^5$ and $R^6$ are each, independently, hydrogen or methyl.

In an embodiment, Y is N and Z is C. In another embodiment, Y is C and Z is N.

In an embodiment, $R^{A1}$ is $C_{3-10}$ cycloalkyl or 4- to 10-membered heterocyclyl, wherein the cycloalkyl and heterocyclyl are unsubstituted or substituted with one, two, or three $R^1$; $R^{A2}$ is H; Y is N; and Z is C.

In another embodiment, $R^{A1}$ is $C_{3-10}$ cycloalkyl or 4- to 10-membered heterocyclyl, wherein the cycloalkyl and heterocyclyl are unsubstituted or substituted with one, two, or three $R^1$; $R^{A2}$ is H; Y is C; and Z is N.

In yet another embodiment, $R^{A1}$ and $R^{A2}$ taken together with the atoms to which they are bound form a $C_{3-10}$ cycloalkyl or a 5- to 10-membered heterocyclyl, wherein the cycloalkyl and heterocyclyl are unsubstituted or substituted with one, two, or three $R^{11}$; Y is N; and Z is C.

In an embodiment, the compound of Formula (I) has a structure according to Formula (I-a):

(I-a)

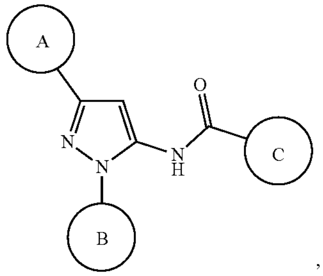

, wherein A is $C_{3-10}$ cycloalkyl or 4- to 10-membered heterocyclyl, wherein the cycloalkyl and heterocyclyl are unsubstituted or substituted with one, two, or three $R^1$.

In another embodiment, the compound of Formula (I) has a structure according to Formula (I-b):

(I-b)

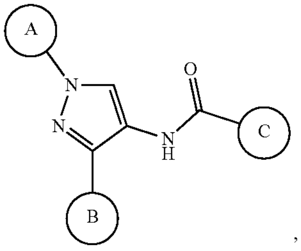

, wherein A is $C_{3-10}$ cycloalkyl or 4- to 10-membered heterocyclyl, wherein the cycloalkyl and heterocyclyl are unsubstituted or substituted with one, two, or three $R^1$.

In yet another embodiment, the compound of Formula (I) has a structure according to Formula (I-c):

(I-c)

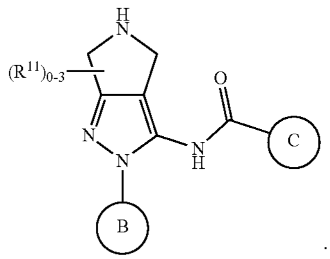

.

In an embodiment, A is $C_{4-6}$ cycloalkyl or 4- to 6-membered heterocyclyl, wherein the cycloalkyl or heterocyclyl are unsubstituted or substituted with one, two, or three $R^1$. In some embodiments, A is a 4- to 6-membered heterocyclyl that is unsubstituted or substituted with one, two, or three $R^1$. In some embodiments, A is a 4- to 6-membered heterocyclyl having 1 or 2 nitrogen atoms and 0 or 1 oxygen atoms, wherein the heterocyclyl is unsubstituted or substituted with one, two, or three $R^1$. In some embodiments, A is piperidinyl that is unsubstituted or substituted with one, two, or three $R^1$. In some embodiments, A is unsubstituted or substituted with one or two $R^1$. In some embodiments, A is substituted with one $R^1$.

In an embodiment, A has the following structure:

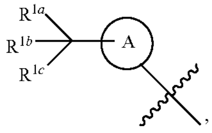

, wherein:

$R^{1a}$ is H or $CH_3$;

$R^{1b}$ is H or $C_{1-3}$ alkyl;

$R^{1c}$ is H or $C_{1-3}$ alkyl; or $R^{1a}$ is H and $R^{1b}$ and $R^{1c}$ taken together form a $C_{3-4}$ cycloalkyl or a 3- to 4-membered heterocyclyl along with the carbon atom to which they are attached.

In another embodiment, A has the following structure:

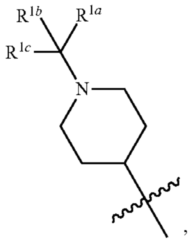, wherein:

$R^{1a}$ is H or $CH_3$;

$R^{1b}$ is H or $C_{1-3}$ alkyl;

$R^{1c}$ is H or $C_{1-3}$ alkyl; or $R^{1a}$ is H and $R^{1b}$ and $R^{1c}$ taken together form a $C_{3-4}$ cycloalkyl or a 3- to 4-membered heterocyclyl along with the carbon atom to which they are attached.

In some embodiments, A is selected from the group consisting of:

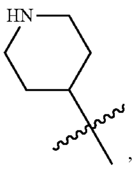, 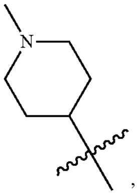, 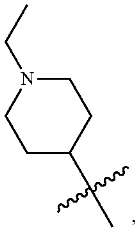, 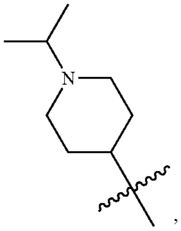, 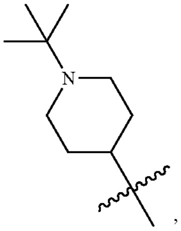, 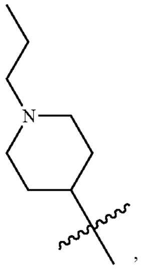, 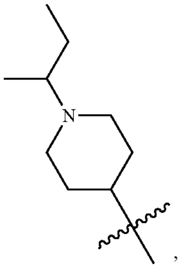, 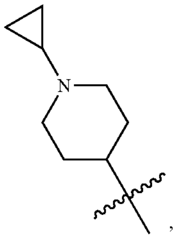, 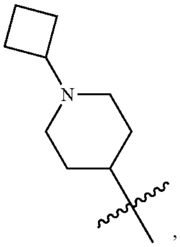, 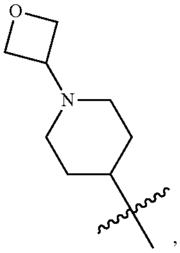, 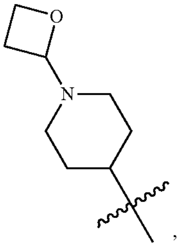, -continued

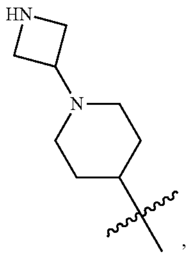, and 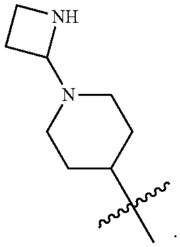.

In some embodiment, A is selected from the group consisting of

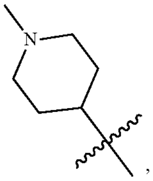, 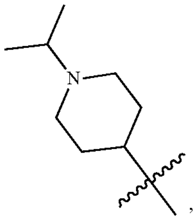, and

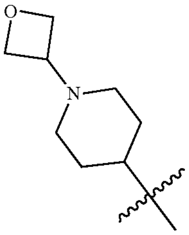.

In an embodiment, the compound of Formula (I) has a structure according to Formula (I-a1):

(I-a1)

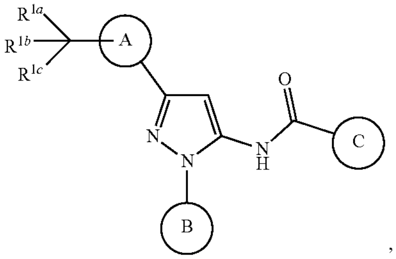, wherein:

$R^{1a}$ is H or $CH_3$;

$R^{1b}$ is H or $C_{1-3}$ alkyl;

$R^{1c}$ is H or $C_{1-3}$ alkyl; or $R^{1a}$ is H and $R^{1b}$ and $R^{1c}$ taken together form a $C_{3-4}$ cycloalkyl or a 3- to 4-membered heterocyclyl along with the carbon atom to which they are attached.

In another embodiment, the compound of Formula (I) has a structure according to Formula (I-a2):

(I-a2)

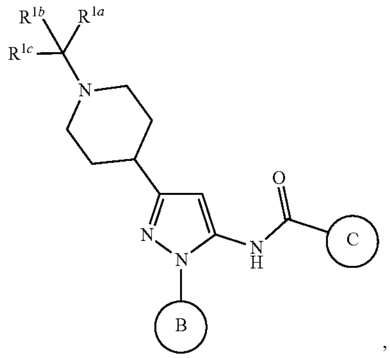

, wherein:

$R^{1a}$ is H or $CH_3$;

$R^{1b}$ is H or $C_{1-3}$ alkyl;

$R^{1c}$ is H or $C_{1-3}$ alkyl; or $R^{1c}$ is H and $R^{1b}$ and $R^{1c}$ taken together form a $C_{3-4}$ cycloalkyl or a 3- to 4-membered heterocyclyl along with the carbon atom to which they are attached.

In another embodiment, the compound of Formula (I) has a structure according to Formula (I-a3):

(I-a3)

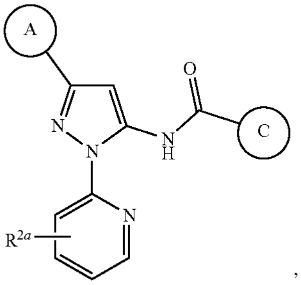

, wherein $R^{2a}$ is H, $C_{1-4}$ alkyl, cyclopropyl, cyclobutyl, —$CF_3$, —$CHF_2$, —$CH_2F$, $C_{1-4}$ alkoxy, halo, or —CN.

In yet another embodiment, the compound of Formula (I) has a structure according to Formula (I-a4):

(I-a4)

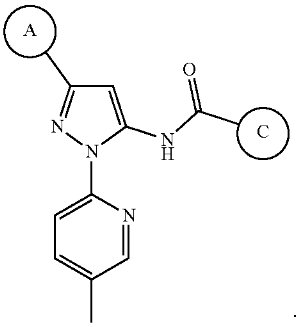

.

In still another embodiment, the compound of Formula (I) has a structure according to Formula (I-a5):

(1-a5)

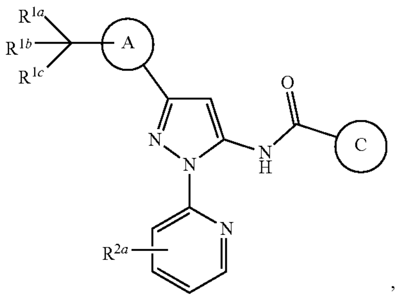

, wherein:

$R^{1a}$ is H or $CH_3$;

$R^{1b}$ is H or $C_{1-3}$ alkyl;

$R^{1c}$ is H or $C_{1-3}$ alkyl; or $R^{1a}$ is H and $R^{1b}$ and $R^{1c}$ taken together form a $C_{3-4}$ cycloalkyl or a 3- to 4-membered heterocyclyl along with the carbon atom to which they are attached; and $R^{2a}$ is H, $C_{1-4}$ alkyl, cyclopropyl, cyclobutyl, —$CF_3$, —$CHF_2$, —$CH_2F$, $C_{1-4}$ alkoxy, halo, or —CN.

In an embodiment the compound of Formula (I) is selected from the group consisting of the compound in Table 1.

TABLE 1

| IRAK4 inhibitors | |
|---|---|
| Structure | Compound No. |
| 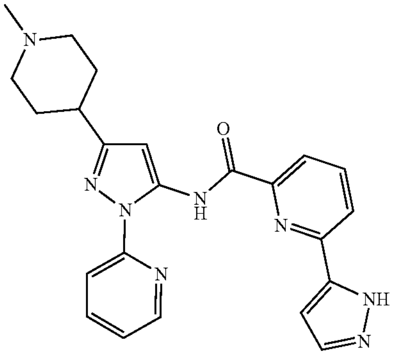 [SMILES: CN1CCC(c2cc(NC(=O)c3cccc(-c4ccn[nH]4)n3)n(-c3ccccn3)n2)CC1] | 001 |
| 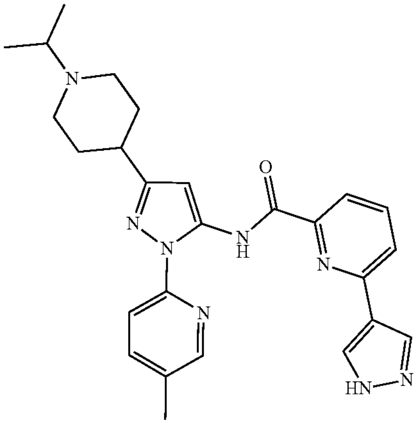 [SMILES: Cc1ccc(-n2nc(C3CCN(C(C)C)CC3)cc2NC(=O)c2cccc(-c3cn[nH]c3)n2)nc1] | 002 |

TABLE 1-continued
| IRAK4 inhibitors | |
|---|---|
| Structure | Compound No. |
| 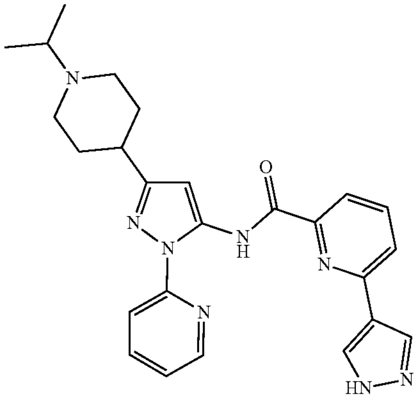 [SMILES: CC(C)N1CCC(c2cc(NC(=O)c3cccc(-c4cn[nH]c4)n3)n(-c3ccccn3)n2)CC1] | 003 |
| 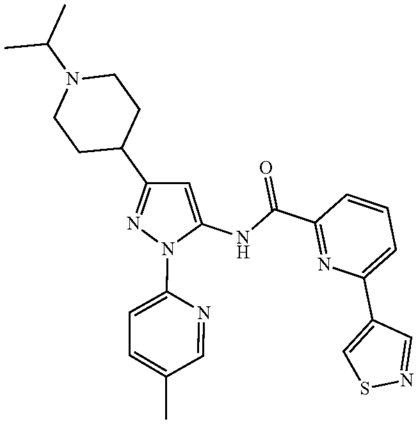 | 004 |
| 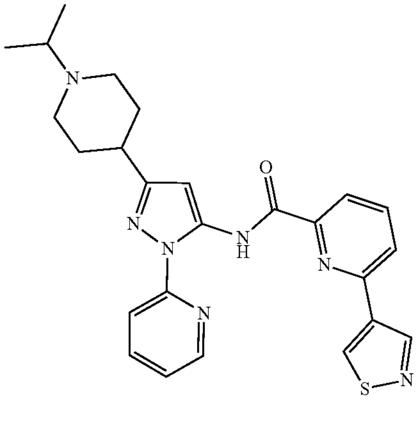 [SMILES: CC(C)N1CCC(c2cc(NC(=O)c3cccc(-c4cnsc4)n3)n(-c3ccccn3)n2)CC1] | 005 |
TABLE 1-continued
| IRAK4 inhibitors | |
|---|---|
| Structure | Compound No. |
| 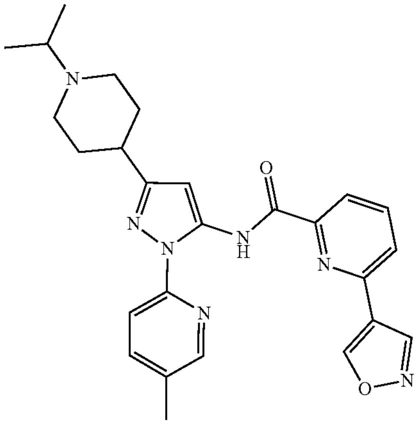 [SMILES: Cc1ccc(-n2nc(C3CCN(C(C)C)CC3)cc2NC(=O)c2cccc(-c3cnoc3)n2)nc1] | 006 |
| 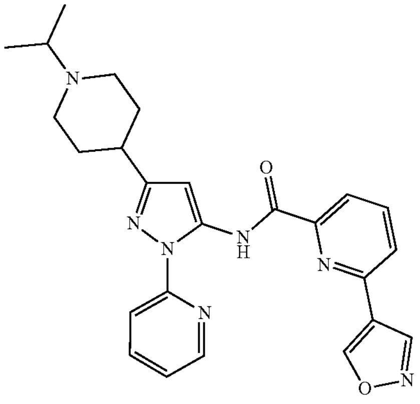 [SMILES: CC(C)N1CCC(c2cc(NC(=O)c3cccc(-c4cnoc4)n3)n(-c3ccccn3)n2)CC1] | 007 |
| 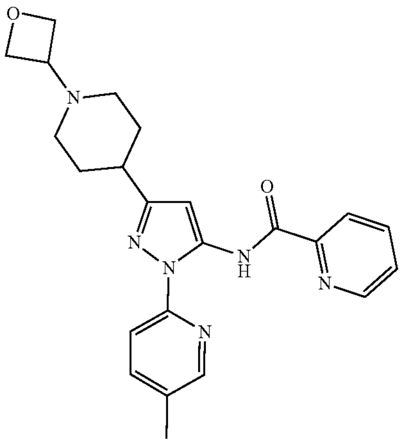 [SMILES: Cc1ccc(-n2nc(C3CCN(C4COC4)CC3)cc2NC(=O)c2ccccn2)nc1] | 008 |

TABLE 1-continued
| IRAK4 inhibitors | |
|---|---|
| Structure | Compound No. |
| 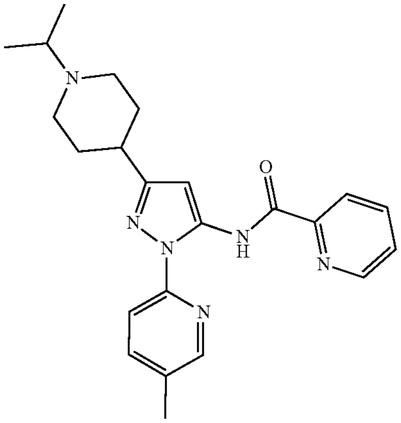 [SMILES: Cc1ccc(-n2nc(C3CCN(C(C)C)CC3)cc2NC(=O)c2ccccn2)nc1] | 009 |
| 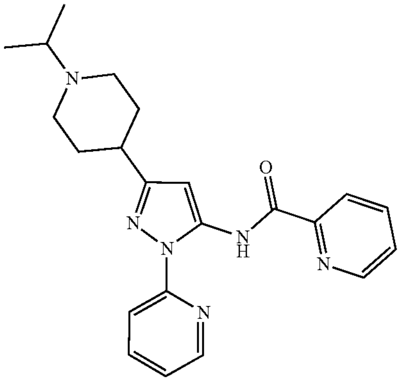 [SMILES: CC(C)N1CCC(c2cc(NC(=O)c3ccccn3)n(-c3ccccn3)n2)CC1] | 010 |
| 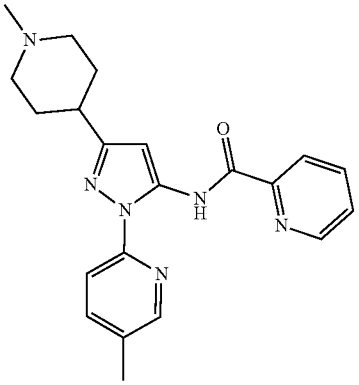 [SMILES: Cc1ccc(-n2nc(C3CCN(C)CC3)cc2NC(=O)c2ccccn2)nc1] | 011 |
TABLE 1-continued
| IRAK4 inhibitors | |
|---|---|
| Structure | Compound No. |
| 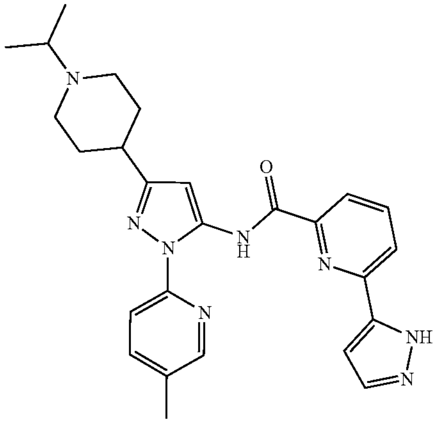 [SMILES: Cc1ccc(-n2nc(C3CCN(C(C)C)CC3)cc2NC(=O)c2cccc(-c3ccn[nH]3)n2)nc1] | 012 |
| 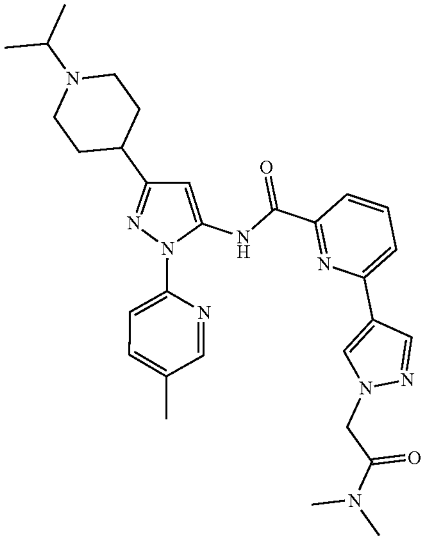 [SMILES: Cc1ccc(-n2nc(C3CCN(C(C)C)CC3)cc2NC(=O)c2cccc(-c3cnn(CC(=O)N(C)C)c3)n2)nc1] | 013 |
| 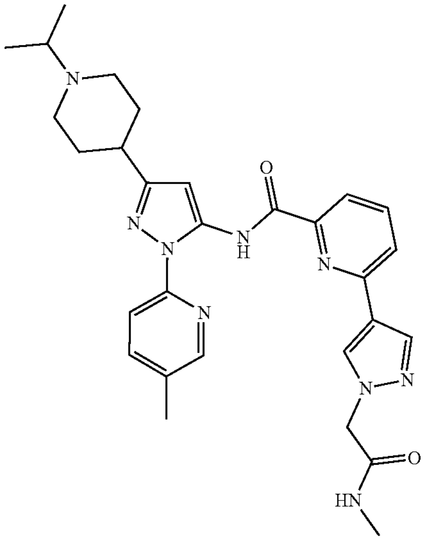 [SMILES: CNC(=O)Cn1cc(-c2cccc(C(=O)Nc3cc(C4CCN(C(C)C)CC4)nn3-c3ccc(C)cn3)n2)cn1] | 014 |

TABLE 1-continued

| IRAK4 inhibitors | |
|---|---|
| Structure | Compound No. |
| 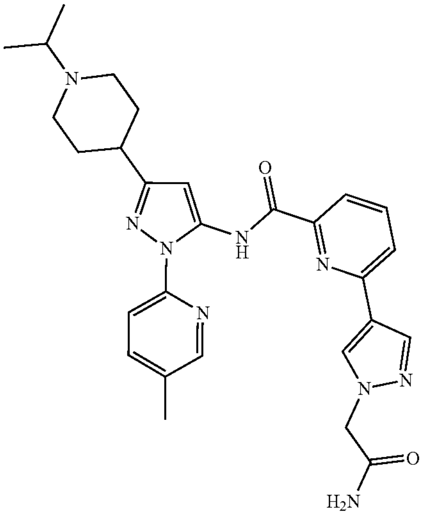 [SMILES: Cc1ccc(-n2nc(C3CCN(C(C)C)CC3)cc2NC(=O)c2cccc(-c3cnn(CC(N)=O)c3)n2)nc1] | 015 |
| 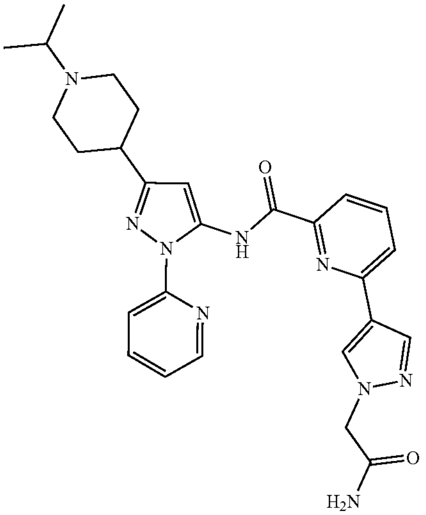 [SMILES: CC(C)N1CCC(c2cc(NC(=O)c3cccc(-c4cnn(CC(N)=O)c4)n3)n(-c3ccccn3)n2)CC1] | 016 |
| 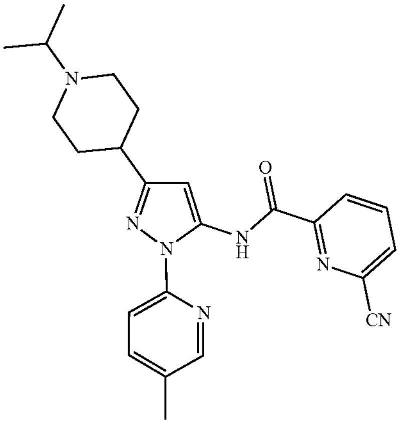 [SMILES: Cc1ccc(-n2nc(C3CCN(C(C)C)CC3)cc2NC(=O)c2cccc(C#N)n2)nc1] | 017 |
| 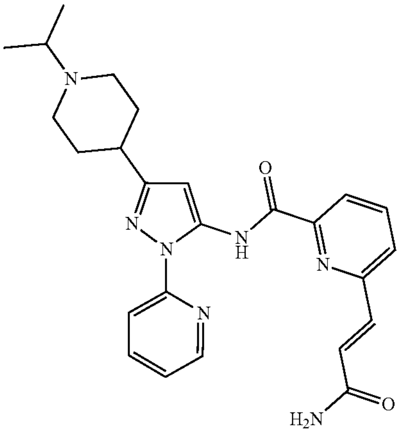 [SMILES: CC(C)N1CCC(c2cc(NC(=O)c3cccc(/C=C/C(N)=O)n3)n(-c3ccccn3)n2)CC1] | 018 |
| 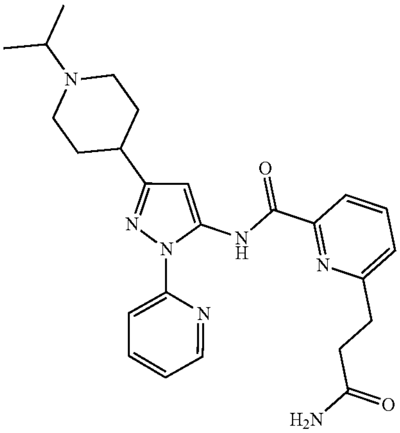 [SMILES: CC(C)N1CCC(c2cc(NC(=O)c3cccc(CCC(N)=O)n3)n(-c3ccccn3)n2)CC1] | 019 |
| 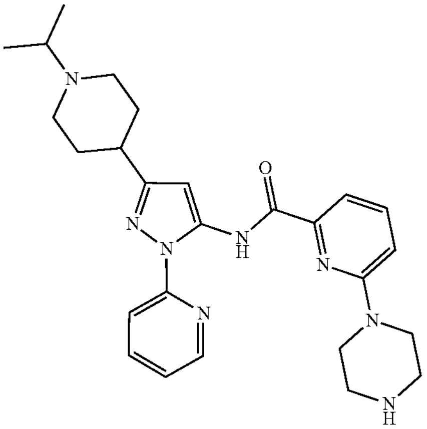 [SMILES: CC(C)N1CCC(c2cc(NC(=O)c3cccc(N4CCNCC4)n3)n(-c3ccccn3)n2)CC1] | 020 |

In an embodiment, a compound of any of the Formulae disclosed herein selectively inhibits IRAK4 over IRAK1. In another embodiment, a compound of any of the Formulae disclosed herein inhibits IRAK4 and has minimal effect on the enzymatic activity of IRAK1.

In an embodiment, the compound is at least 2-fold more selective for IRAK4 than for IRAK1. In another embodiment, the compound is at least 5-fold more selective for IRAK4 than for IRAK1. In yet another embodiment, the compound is at least 7-fold more selective for IRAK4 than for IRAK1. In still another embodiment, the compound is at least 10-fold more selective for IRAK4 than for IRAK1.

In an embodiment, the compound is at least 15-fold more selective for IRAK4 than for IRAK1. In another embodiment, the compound is at least 20-fold more selective for IRAK4 than for IRAK1. In yet another embodiment, the compound is at least 25-fold more selective for IRAK4 than for IRAK1. In still another embodiment, the compound is at least 30-fold more selective for IRAK4 than for IRAK1.

The compounds disclosed herein may exist as tautomers and optical isomers (e.g., enantiomers, diastereomers, diastereomeric mixtures, racemic mixtures, and the like).

Furthermore, the compounds disclosed herein may comprise any isotope or isotopic mixture of the atoms contained therein. Said isotopes and isotopic mixtures may be naturally occurring or synthetically produced, either with natural abundance or in an isotopically enriched form. For example, a reference to hydrogen includes within its scope $^{1}H$, $^{2}H$ (D), and $^{3}H$ (T). In some embodiments, the compounds described herein include a $^{2}H$ (i.e., deuterium) isotope.

It is generally well known in the art that any compound that will be converted in vivo to provide a compound of Formula (I) is a prodrug within the scope of the present disclosure.

In an aspect, provided herein is a pharmaceutical composition comprising a compound disclosed herein, or a pharmaceutically acceptable salt thereof, and a pharmaceutically acceptable carrier.

In another aspect, the pharmaceutical composition further comprises a second active agent. In some embodiments, the second active agent is a kinase inhibitor. In further embodiments, the second pharmaceutical agent is a Bruton's tyrosine kinase (BTK) inhibitor.

In yet another aspect, the present disclosure provides pharmaceutical compositions including a compound described herein, and optionally a pharmaceutically acceptable excipient.

In an embodiment, the pharmaceutical compositions described herein include a therapeutically or prophylactically effective amount of a compound described herein. The pharmaceutical composition may be useful for treating a proliferative disease in a subject in need thereof, preventing a proliferative disease in a subject in need thereof, or inhibiting the activity of a protein kinase (e.g., IRAK4) in a subject, biological sample, tissue, or cell. In certain embodiments, the proliferative disease is cancer (e.g., lymphoma, leukemia, or myelodysplastic syndrome (MDS)). In certain embodiments, the proliferative disease is an inflammatory disease. In certain embodiments, the inflammatory disease is rheumatoid arthritis, Crohn's disease, or fibrosis. In certain embodiments, the proliferative disease is an autoimmune disease.

Methods of Treatment

In an aspect, provided herein is a method of treating cancer in an individual in need thereof, comprising administering to the individual a therapeutically effective amount of a compound of the disclosure. In an embodiment, the cancer is selected from the group consisting of lung cancer, colon cancer, breast cancer, endometrial cancer, thyroid cancer, glioma, squamous cell carcinoma, and prostate cancer. In another embodiment, the cancer is non-small cell lung cancer (NSCLC). In another embodiment, the cancer is selected from the group consisting of human myelodysplastic syndrome (MDS), leukemia, breast cancer, and lymphoma.

In another aspect, provided herein is a method of inhibiting a kinase in an individual in need thereof, comprising administering to the individual a therapeutically effective amount of a compound of the disclosure. In an embodiment, the kinase is IRAK. In another embodiment, the kinase is IRAK4.

In another aspect, the present disclosure provides methods for treating and/or preventing a proliferative disease. Exemplary proliferative diseases that may be treated include diseases associated with the overexpression or increased activity of an interleukin-1 receptor-associated kinase (IRAK), e.g., cancer, benign neoplasms, diseases associated with angiogenesis, inflammatory diseases, autoinflammatory diseases, and autoimmune diseases. In certain embodiments, the cancer is selected from the group consisting of pancreatic cancer, lung cancer (e.g., small cell lung cancer (SCLC), non-small cell lung cancer), prostate cancer, breast cancer, ovarian cancer, kidney cancer, liver cancer, Ewing's sarcoma, myeloma, Waldenstrom's macroglobulinemia, myelodysplastic syndrome (MDS), osteosarcoma, brain cancer, neuroblastoma, and colorectal cancer.

In another aspect, provided herein is a method of inhibiting the activity of a kinase (e.g., IRAK (e.g., IRAK4)) using a compound described herein in a biological sample or subject. In certain embodiments, the method involves the selective inhibition of IRAK4.

The present disclosure also provides methods of inhibiting cell growth in a biological sample or subject, the method comprising contacting the biological sample or subject with an effective amount of a compound disclosed herein. In still another aspect, the present invention provides methods of inducing apoptosis of a cell in a biological sample or subject, the method comprising contacting the biological sample or subject with an effective amount of a compound disclosed herein.

The present disclosure provides methods for administering to a subject in need thereof an effective amount of a compound, or pharmaceutical composition thereof, as described herein. Also described are methods for contacting a cell with an effective amount of a compound, or pharmaceutical composition thereof, as described herein. In certain embodiments, a method described herein further includes administering to the subject an additional pharmaceutical agent. In certain embodiments, a method described herein further includes contacting the cell with an additional pharmaceutical agent (e.g., an antiproliferative agent). In certain embodiments, the additional pharmaceutical agent is a kinase inhibitor (e.g., an inhibitor of Bruton's tyrosine kinase (BTK)). The methods described herein may further include performing radiotherapy, immunotherapy, and/or transplantation on the subject.

In yet another aspect, provided herein is a method of treating or preventing a kinase-mediated disorder in an individual in need thereof, comprising administering to the individual a therapeutically effective amount of a compound of the disclosure.

Modulation of IRAK provides an approach to the treatment, prevention, or amelioration of diseases including, but not limited to, cancer and metastasis, inflammation, arthritis, systemic lupus erythematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In some embodiments, the compounds of the disclosure exhibit inhibition of IRAK4 and exhibit minimal, if any, effect on the enzymatic activity of IRAK1. In certain embodiments, the compounds of the disclosure exhibit at least 2-fold, 5-fold, 7-fold, 10-fold, 15-fold, 20-fold, 25-fold, or 30-fold greater inhibition for IRAK4 than for IRAK1.

In some embodiments, the compounds of the disclosure exhibit at least 2-fold greater inhibition for IRAK4 than for IRAK1. In some embodiments, the compounds of the disclosure exhibit at least 5-fold greater inhibition for IRAK4 than for IRAK1. In some embodiments, the compounds of the disclosure exhibit at least 7-fold greater inhibition for IRAK4 than for IRAK1. In some embodiments, the compounds of the disclosure exhibit at least 10-fold greater inhibition for IRAK4 than for IRAK1.

In some embodiments, the compounds of the disclosure exhibit at least 15-fold greater inhibition for IRAK4 than for IRAK1. In some embodiments, the compounds of the disclosure exhibit at least 20-fold greater inhibition for IRAK4 than for IRAK1. In some embodiments, the compounds of the disclosure exhibit at least 25-fold greater inhibition for IRAK4 than for IRAK1. In some embodiments, the compounds of the disclosure exhibit at least 30-fold greater inhibition for IRAK4 than for IRAK1.

In some embodiments, the inhibition of IRAK activity is measured by $IC_{50}$.

In some embodiments, the inhibition of IRAK activity is measured by $EC_{50}$.

In some embodiments, the inhibition of IRAK by a compound of the disclosure can be measured via a biochemical assay. By illustrative and non-limiting example, a homogenous time-resolved fluorescence (HTRF) assay may be used to determine inhibition of IRAK activity using conditions and experimental parameters disclosed herein. The HTRF assay may, for example, employ concentrations of substrate (e.g., biotin-Lck-peptide substrate) of about 1 μM; concentrations of IRAK from about 0.2 nM to about 40 nM; and concentrations of inhibitor from about 0.000282 μM to about 50 μM. A compound of the disclosure screened under these conditions may, for example, exhibit an $IC_{50}$ value from about 1 nM to >1 μM; from about 1 nM to about 400 nM; from about 1 nM to about 150 nM; from about 1 nM to about 75 nM; from about 1 nM to about 40 nM; from about 1 nM to about 25 nM; from about 1 nM to about 15 nM; or from about 1 nM to about 10 nM.

Potency of the inhibitor can be determined by $EC_{50}$ value. A compound with a lower $EC_{50}$ value, as determined under substantially similar conditions, is a more potent inhibitor relative to a compound with a higher $EC_{50}$ value.

Potency of the inhibitor can also be determined by $IC_{50}$ value. A compound with a lower $IC_{50}$ value, as determined under substantially similar conditions, is a more potent inhibitor relative to a compound with a higher $IC_{50}$ value.

The selectivity between IRAK4 and IRAK1 can also be measured using cellular proliferation assays where cell proliferation is dependent on kinase activity. Proliferation assays are performed at a range of inhibitor concentrations (10 μM, 3 μM, 1.1 μM, 330 nM, 110 nM, 33 nM, 11 nM, 3 nM, 1 nM) and an $EC_{50}$ is calculated.

In still another aspect, the disclosure provides a method of treating a disease or disorder associated with overexpression of IRAK4, aberrant activity of IRAK4, or increased activity of IRAK4, the method comprising administering to a subject in need thereof an effective amount of a compound of disclosed herein, or a pharmaceutically acceptable salt thereof. In some embodiments, the method further comprises administering a second pharmaceutical agent. In some embodiments, the second pharmaceutical agent is an antibody. In another embodiment, the second pharmaceutical agent is a kinase inhibitor. In yet another embodiment, the second pharmaceutical agent is a Bruton's tyrosine kinase (BTK) inhibitor.

The additional pharmaceutical agents include, but are not limited to, antiproliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent).

In certain embodiments, the additional pharmaceutical agent is ibrutinib. In certain embodiments, the additional pharmaceutical agent is a protein kinase inhibitor (e.g., tyrosine protein kinase inhibitor). In certain embodiments, the additional pharmaceutical agent is a binder or inhibitor of an IRAK (e.g., IRAK1 or IRAK4). In certain embodiments, the additional pharmaceutical agent is a binder or inhibitor of IRAK1. In certain embodiments, the additional pharmaceutical agent is a binder or inhibitor of IRAK4. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

In certain embodiments, the disease is cancer or a proliferation disease.

In further embodiments, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer. In some embodiments, the disease is human myelodysplastic syndrome (MDS), leukemia, breast cancer, or lymphoma. In certain embodiments, the disease is triple-negative breast cancer, acute myeloid leukemia (AML), diffuse large B cell lymphoma, or Waldenström macroglobulinemia.

In yet another aspect, provided herein is a method of treating a kinase-mediated disorder comprising administering to a subject in need thereof an effective amount of a compound disclosed herein, or a pharmaceutically acceptable salt thereof. In some embodiments, the kinase is IRAK4. In other embodiments, the subject is administered an additional therapeutic agent. In other embodiments, the compound and the additional therapeutic agent are administered simultaneously or sequentially.

In other embodiments, the disease is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer. In some embodiments, the disease is human myelodysplastic syndrome (MDS), leukemia, breast cancer, or lymphoma. In certain embodiments, the disease is triple-negative breast cancer, acute myeloid leukemia (AML), diffuse large B cell lymphoma, or Waldenström macroglobulinemia.

In some embodiments, the disease is triple-negative breast cancer. In some embodiments, the disease is acute myeloid leukemia (AML). In some embodiments, the disease is an activated B cell lymphoma. In some embodiments, the disease is diffuse large B cell lymphoma. In some embodiments, the disease is Waldenström macroglobulinemia.

In an embodiment of the methods disclosed herein, the subject is a human.

In another aspect, the disclosure provides a compound disclosed herein, or a pharmaceutically acceptable salt thereof, for use in the manufacture of a medicament for treating or preventing a disease in which IRAK (e.g., IRAK4) plays a role.

In an aspect, provided herein is a method of treating or preventing a condition selected from the group consisting of autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

In certain embodiments, the proliferative disease to be treated or prevented using the compounds described herein may be associated with the overexpression of an IRAK (e.g., IRAK4).

A proliferative disease may be associated with aberrant activity of an IRAK (e.g., IRAK4). Aberrant activity of an IRAK (e.g., IRAK4) may be elevated and/or inappropriate or undesired activity of the IRAK. Deregulation of cell cycle progression is a characteristic of a proliferative disease, and a majority of proliferative diseases have abnormalities in some component of IRAK (e.g., IRAK4) activity, frequently through elevated and/or inappropriate IRAK activation. In certain embodiments, IRAK is not overexpressed, and the activity of IRAK is elevated and/or inappropriate. In certain embodiments, IRAK4 is overexpressed, and the activity of IRAK4 is elevated and/or inappropriate.

One aspect of this disclosure provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, colorectal, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colonrectum, large intestine, rectum, brain and central nervous system, chronic myeloid leukemia (CML), and leukemia. The term "cancer" includes, but is not limited to, the following cancers: myeloma, lymphoma, or a cancer selected from gastric, renal, head and neck, oropharangeal, non-small cell lung cancer (NSCLC), endometrial, hepatocarcinoma, non-Hodgkin's lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodysplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the disclosure, the present disclosure provides for the use of one or more compounds of the disclosure in the manufacture of a medicament for the treatment of cancer, including without limitation the various types of cancer disclosed herein.

In some embodiments, the compounds of this disclosure are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this disclosure are useful for treating hematopoietic disorders acute-myelogenous leukemia (AML), chronic-myelogenous leukemia (CML), acute-promyelocytic leukemia, and acute lymphocytic leukemia (ALL).

In some embodiments, the compounds of this disclosure are useful for treating human myelodysplastic syndrome (MDS), leukemia, breast cancer, and lymphoma. In some embodiments, the compounds of this disclosure are useful for treating triple-negative breast cancer. In some embodiments, the compounds of this disclosure are useful for treating acute myeloid leukemia (AML). In some embodiments, the compounds of this disclosure are useful for treating an activated B cell lymphoma (e.g., diffuse large B cell lymphoma). In some embodiments, the compounds of this disclosure are useful for treating Waldenström macroglobulinemia.

The term "cancerous cell" as provided herein, includes a cell afflicted by any one of the above-identified conditions.

The disclosure further provides a method for the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias, or pre-cancerous lesions from continuing to expand or from becoming cancerous. Examples of pre-cancerous lesions may occur in skin, esophageal tissue, breast and cervical intra-epithelial tissue.

Examples of neurodegenerative diseases include, without limitation, adrenoleukodystrophy (ALD), Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease (spinocerebellar ataxia type 3), multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease (also known as Batten disease), spinocerebellar ataxia (multiple types with varying characteristics), spinal muscular atrophy, Steele-Richardson-Olszewski disease, tabes dorsalis, and toxic encephalopathy.

Another aspect of this disclosure provides a method for the treatment or lessening the severity of a disease selected from a proliferative or hyperproliterative disease, or a neurodegenerative disease, comprising administering an effective amount of a compound, or a pharmaceutically acceptable composition comprising a compound, to a subject in need thereof.

The activity of the compounds and compositions of the present disclosure as IRAK4 inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this disclosure as an inhibitor of various kinases are set forth in the Examples below.

In accordance with the foregoing, the present disclosure further provides a method for preventing or treating any of the diseases or disorders described above in a subject in need of such treatment, which method comprises administering to said subject a therapeutically effective amount of a compound of the disclosure, or a pharmaceutically acceptable salt thereof, and optionally a second active agent. For any of the above uses, the required dosage will vary depending on the mode of administration, the particular condition to be treated and the effect desired.

Administration/Dosages/Formulations

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations (for example, sterile injectable aqueous or oleaginous suspensions) may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising (a) a first agent which is a compound of the disclosure as disclosed herein, in free form or in pharmaceutically acceptable salt form, and (b) at least one co-agent. The kit can comprise instructions for its administration.

In certain embodiments, these compositions optionally further comprise one or more additional therapeutic agents. For example, a Bruton's tyrosine kinase (BTK) inhibitor, chemotherapeutic agents, or other antiproliferative agents may be combined with the compounds of this disclosure to treat proliferative diseases and cancer.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic acid, or potassium sorbate; partial glyceride mixtures of saturated vegetable fatty acids; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

Kits

In an aspect, provided herein is a kit comprising a compound capable of inhibiting kinase activity selected from one or more compounds of disclosed herein, or pharmaceutically acceptable salts thereof, and instructions for use in treating cancer.

In another aspect, provided herein is a kit comprising a compound capable of inhibiting IRAK4 activity selected from a compound disclosed herein, or a pharmaceutically acceptable salt thereof.

In another aspect, the disclosure provides a kit comprising a compound capable of inhibiting kinase activity selected from one or more compounds of disclosed herein, or pharmaceutically acceptable salts thereof; a second active agent; and instructions for use in treating cancer. In some embodiments, the second active agent is a Bruton's tyrosine kinase (BTK) inhibitor. In an embodiment, the BTK inhibitor is ibrutinib. In another embodiment, the BTK inhibitor is acalabrutinib. In yet another embodiment, the BTK inhibitor is zanubrutinib.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations

AcOH acetic acid
dba dibenzylideneacetone
DCE 1,2-dichloroethane
DCM dichloromethane
DIEA diisopropylethylamine
DMF N,N-dimethylformamide
DMSO dimethylsulfoxide
dppf Bis(diphenylphosphino)ferrocene
HATU 1-[Bis(dimethylamino)methylene]-1H-1,2,3-triazolo[4,5-b]pyridinium 3-oxide hexafluorophosphate
iPrOH isopropyl alcohol
STAB sodium triacetoxyborohydride
t-BuXPhos 2-di-tert-butylphosphino-2',4',6'-triisopropylbiphenyl
TFA trifluoroacetic acid
THF tetrahydrofuran
Xantphos 4,5-Bis(diphenylphosphino)-9,9-dimethylxanthene

Example 1: Preparation of Compounds 001 to 013

Scheme 1.

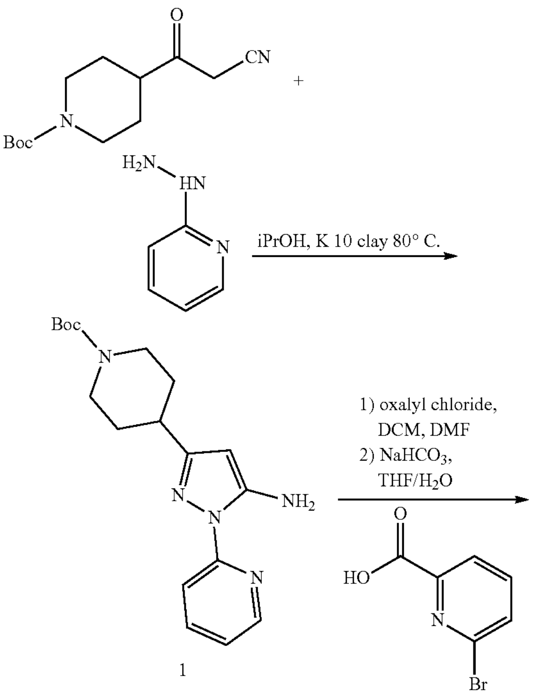

1

-continued

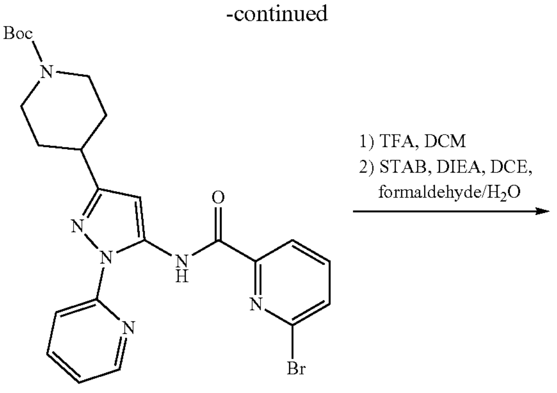

2

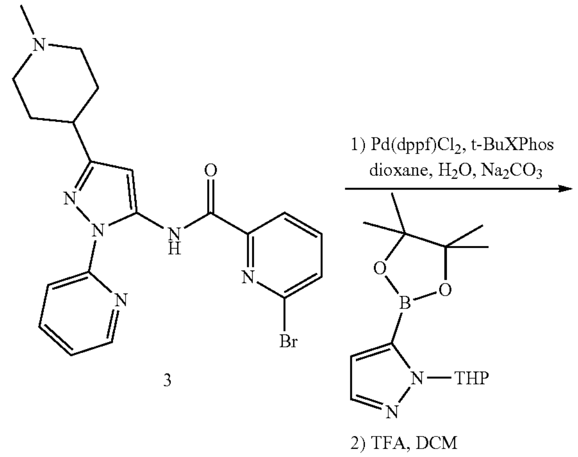

3

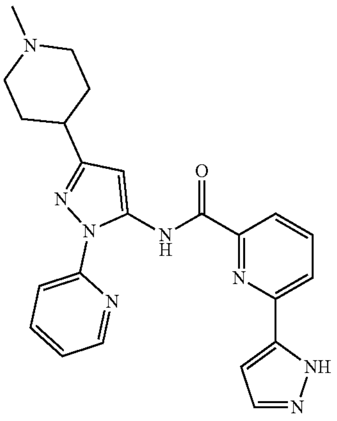

001 tert-Butyl 4-(5-amino-1-(pyridin-2-yl)-1H-pyrazol-3-yl)piperidine-1-carboxylate (1)

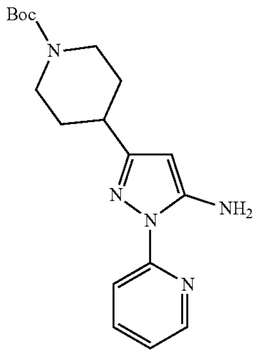 [SMILES: CC(C)(C)OC(=O)N1CCC(c2cc(N)n(-c3ccccn3)n2)CC1]

To a solution of tert-butyl 4-(2-cyanoacetyl)piperidine-1-carboxylate (3 g, 11.89 mmol) and 2-hydrazineylpyridine (1.48 g, 12.00 mmol) in iPrOH (200 mL) was added montmorillonite K 10 clay (4 g). The mixture was refluxed for 2 days. Afterward, the mixture was filtered, concentrated, dissolved in EtOAc, washed with 1M NaOH, brine, dried over $MgSO_4$ and condensed to give a beige solid that was used without further purification. m/z ESI expected: 343.43, observed: 344.71.

tert-Butyl 4-(5-(6-bromopicolinamido)-1-(pyridin-2-yl)-1H-pyrazol-3-yl)piperidine-1-carboxylate (2)

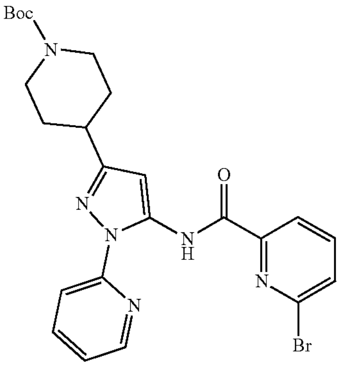 [SMILES: CC(C)(C)OC(=O)N1CCC(c2cc(NC(=O)c3cccc(Br)n3)n(-c3ccccn3)n2)CC1]

To a solution of 6-bromopicolinic acid (947 mg, 7.7 mmol) in DCM (50 mL) was added oxalyl chloride (3 mL, 35 mmol) followed by DMF (3 drops). The reaction was stirred at room temperature for 1 hr. The solvent was removed and the residue dissolved in THE (20 mL). tert-butyl 4-(5-amino-1-(pyridin-2-yl)-1H-pyrazol-3-yl)piperidine-1-carboxylate (1, 2.5 g, 7 mmol) in THE (50 mL) was added followed by saturated aqueous $NaHCO_3$ (10 mL). The reaction was stirred for 30 minutes, quenched with $H_2O$, extracted with EtOAc, dried over $MgSO_4$, and condensed to give a brown oil that was purified by flash chromatography using a gradient of 10 to 60% EtOAc in hexanes to give the desired product as a white solid 2.64 g, 70% yield. m/z ESI expected: 527.42, observed: 528.37.

6-Bromo-N-(3-(1-methylpiperidin-4-yl)-1-(pyridin-2-yl)-1H-pyrazol-5-yl)picolinamide (3)

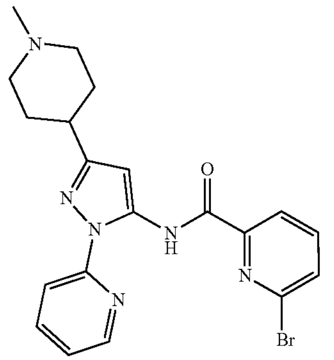 [SMILES: CN1CCC(c2cc(NC(=O)c3cccc(Br)n3)n(-c3ccccn3)n2)CC1]

To a solution of 6-bromo-N-(3-(1-methylpiperidin-4-yl)-1-(pyridin-2-yl)-1H-pyrazol-5-yl)picolinamide (2, 100 mg, 0.216 mmol) in DCM (10 mL) was added TFA (1 mL), and the mixture stirred for 1 hr. The solvent was removed, and the residue was dissolved in DCE (10 mL). To the mixture was added DIEA (188 μL, 1.08 mmol) followed by formaldehyde (37 wt. % in $H_2O$, 53 μL, 0.648 mmol), and the mixture was stirred for 10 minutes. Sodium triacetoxyborohydride (140 mg, 0.659 mmol) was added and the mixture was stirred overnight. The mixture was quenched with saturated aqueous $NaHCO_3$ extracted with DCM, dried over $MgSO_4$ and condensed to give a gray solid that was used without further purification. Yield: quantitative. m/z ESI expected: 441.33, observed: 442.53.

N-(3-(1-Methylpiperidin-4-yl)-1-(pyridin-2-yl)-1H-pyrazol-5-yl)-6-(1H-pyrazol-5-yl)picolinamide (001)

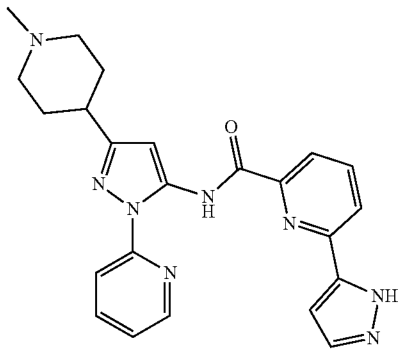 [SMILES: CN1CCC(c2cc(NC(=O)c3cccc(-c4ccn[nH]4)n3)n(-c3ccccn3)n2)CC1]

To a solution of 6-bromo-N-(1-(5-methylpyridin-2-yl)-3-(1-(oxetan-3-yl)piperidin-4-yl)-1H-pyrazol-5-yl)picolinamide (3, 100 mg, 0.23 mmol) in 1,4-dioxane (5 mL) was added 1-(tetrahydro-2H-pyran-2-yl)-5-(4,4,5,5-tetramethyl-1,3,2-dioxaborolan-2-yl)-1H-pyrazole (69 mg, 0.25 mmol) followed by $Na_2CO_3$ (2M aqueous solution, 0.6 mL, 1.13 mmol). The mixture was degassed in a sonicator for 2 minutes. Pd(dppf)$Cl_2$ (10 mg, 0.014 mmol) and t-BuXPhos (8 mg, 0.018 mmol) were added, and the mixture was heated to 90° C. in a sealed vial for 1 hour. The reaction was quenched with water (10 mL) and extracted with EtOAC (2×50 mL), washed with brine, dried over $MgSO_4$, and condensed. The crude material was dissolved in DCM (10 mL) and TFA (1 mL) was added. The mixture was stirred for 60 minutes and the solvent removed in vacuo. The crude material was purified by reversed phase HPLC to give the desired compound as a beige solid (29 mg, 30% yield). m/z expected: 428.5, observed: 429.62.

N-(3-(1-isopropylpiperidin-4-yl)-1-(5-methylpyridin-2-yl)-1H-pyrazol-5-yl)-6-(1H-pyrazol-4-yl)picolinamide (002)

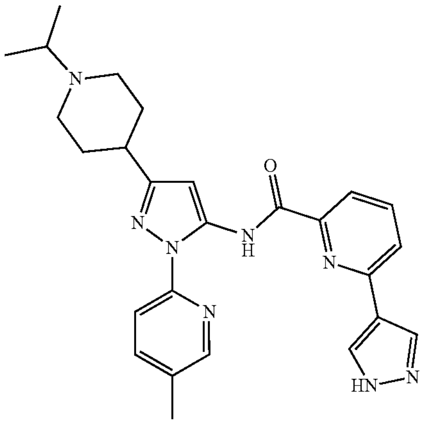 [SMILES: Cc1ccc(-n2nc(C3CCN(C(C)C)CC3)cc2NC(=O)c2cccc(-c3cn[nH]c3)n2)nc1]

The same procedure for 001 was followed to give 15 mg of a white solid in 38% yield. m/z ESI expected: 470.58, observed: 471.23.

N-(3-(1-isopropylpiperidin-4-yl)-1-(pyridin-2-yl)-1H-pyrazol-5-yl)-6-(1H-pyrazol-4-yl)picolinamide (003)

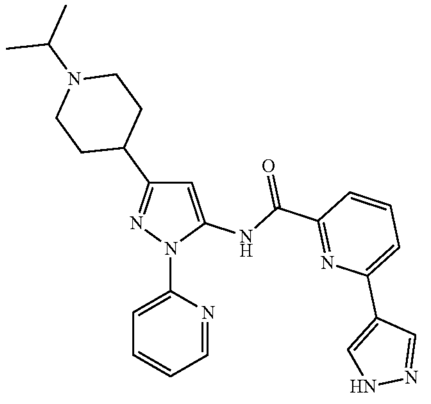 [SMILES: CC(C)N1CCC(c2cc(NC(=O)c3cccc(-c4cn[nH]c4)n3)n(-c3ccccn3)n2)CC1]

The same procedure for 001 was followed to give 15 mg of a white solid in 38% yield. m/z ESI expected: 456.55, observed: 457.49; $^1H$ NMR (500 MHz DMSO) δ 10.19 (Br, 1H), 8.67 (d, J=5 Hz, 1H), 8.25-8.21 (m, 1H), 8.17-8.08 (m, 3H), 8.03-7.98 (m, 2H), 7.45-7.41 (m, 1H), 7.08 (d, J=3 Hz, 1H), 6.99 (s, 1H), 3.52-3.43 (m, 4H), 3.16-3.09 (m, 2H), 3.04 (sept, J=5 Hz, 1H), 2.27-2.10 (m, 4H), 1.32 (d, J=7 Hz, 6H).

N-(3-(1-isopropylpiperidin-4-yl)-1-(5-methylpyridin-2-yl)-1H-pyrazol-5-yl)-6-(isothiazol-4-yl)picolinamide (004)

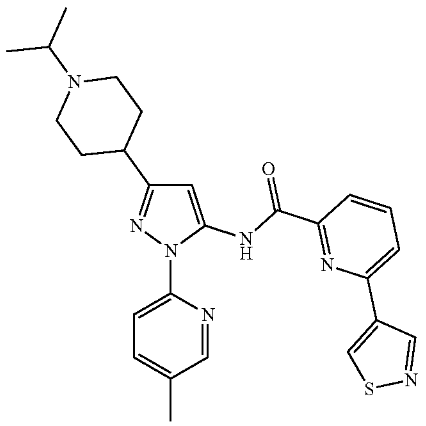 [SMILES: Cc1ccc(-n2nc(C3CCN(C(C)C)CC3)cc2NC(=O)c2cccc(-c3cnsc3)n2)nc1]

The same procedure for 001 was followed to give 16 mg of a white solid in 40% yield. m/z ESI expected: 487.63, observed: 488.72; $^{1}$H NMR (500 MHz, DMSO) δ 9.74 (s, 1H), 9.37 (s, 1H), 8.25 (dd, J=7.7, 1.1 Hz, 2H), 8.20 (t, J=7.7 Hz, 1H), 8.12 (dd, J=7.7, 1.0 Hz, 1H), 7.92-7.88 (m, 2H), 6.95 (s, 1H), 3.17-3.11 (m, 2H), 3.06-3.01 (m, 1H), 2.34 (s, 3H), 2.27-2.24 (m, 2H), 2.00-1.92 (m, 2H), 1.30 (d, J=6.7 Hz, 6H), 1.24 (d, J=6.7 Hz, 1H).

N-(3-(1-isopropylpiperidin-4-yl)-1-(pyridin-2-yl)-1H-pyrazol-5-yl)-6-(isothiazol-4-yl)picolinamide (005)

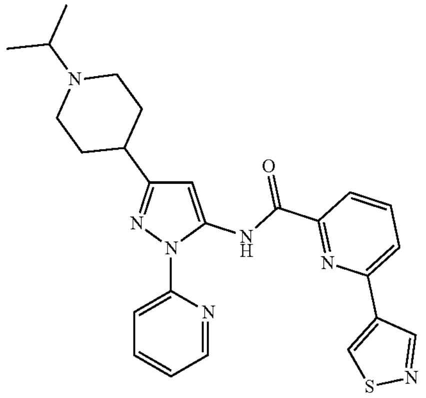 [SMILES: CC(C)N1CCC(c2cc(NC(=O)c3cccc(-c4cnsc4)n3)n(-c3ccccn3)n2)CC1]

The same procedure for 001 was followed to give 27 mg of a white solid in 54% yield. m/z ESI expected: 457.54, observed: 458.47; 1H NMR (500 MHz DMSO) δ 9.77 (s, 1H), 9.41 (s, 1H), 8.48 (d, J=5 Hz, 1H), 8.30-8.20 (m, 2H), 8.17-7.99 (m, 3H), 7.48-7.44 7.01 (s, 1H), 3.22-3.11 (m, 6H), 3.04 (sept, J=5 Hz, 1H), 2.31-2.23 (m, 3H), 2.03-1.91 (m, 2H), 1.31 (d, J=7 Hz, 6H).

N-(3-(1-isopropylpiperidin-4-yl)-1-(5-methylpyridin-2-yl)-1H-pyrazol-5-yl)-6-(isoxazol-4-yl)picolinamide (006)

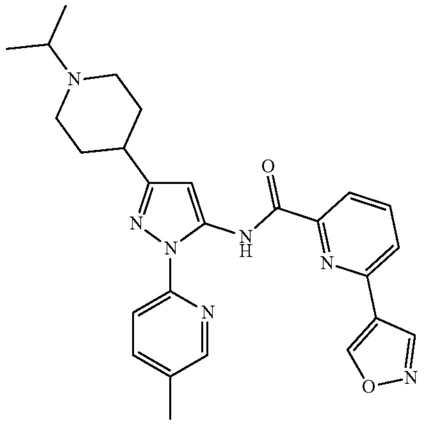 [SMILES: Cc1ccc(-n2nc(C3CCN(C(C)C)CC3)cc2NC(=O)c2cccc(-c3cnoc3)n2)nc1]

The same procedure for 001 was followed to give 6 mg of a white solid in 15% yield. m/z ESI expected: 471.57, observed: 472.47; $^{1}$H NMR (500 MHz DMSO) δ 8.65 (s, 1H), 8.41 (s, 1H), 8.09-7.99 (m, 2H), 7.91-7.83 (m, 2H), 7.73-7.71 (m, 1H), 6.95 (s, 1H), 3.19-3.1 (m, 6H), 3.03 (sept, J=5 Hz, 1H), 2.36 (s, 3H), 2.3-1.91 (m, 5H), 1.30 (d, J=7 Hz, 6H).

N-(3-(1-isopropylpiperidin-4-yl)-1-(pyridin-2-yl)-1H-pyrazol-5-yl)-6-(isoxazol-4-yl)picolinamide (007)

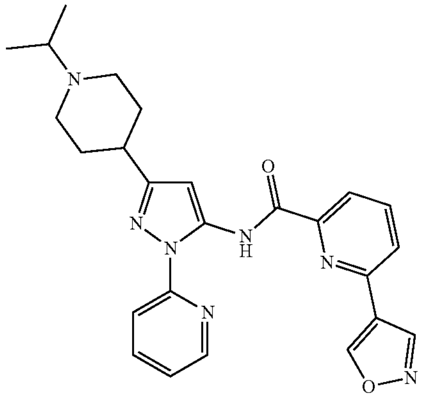 [SMILES: CC(C)N1CCC(c2cc(NC(=O)c3cccc(-c4cnoc4)n3)n(-c3ccccn3)n2)CC1]

The same procedure for 001 was followed to give 8 mg of a white solid in 21% yield. m/z ESI expected: 457.54, observed: 458.47; $^{1}$H NMR (500 MHz DMSO) δ 9.71 (s, 1H), 9.28 (s, 1H), 8.43 (d, J=5 Hz, 1H), 8.23-8.19 (m, 1H), 8.15-8.08 (m, 3H), 8.03-7.98 (m, 1H), 7.47-7.45 (m, 1H), 6.98 (s, 1H), 3.20-3.0 (m, 6H), 3.05 (sept, J=5 Hz, 1H), 2.31-1.91 (m, 5H), 1.30 (d, J=7 Hz, 6H).

N-(1-(5-methylpyridin-2-yl)-3-(1-(oxetan-3-yl)piperidin-4-yl)-1H-pyrazol-5-yl)picolinamide (008)

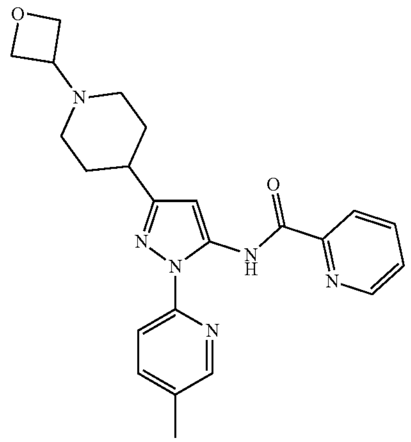 [SMILES: Cc1ccc(-n2nc(C3CCN(C4COC4)CC3)cc2NC(=O)c2ccccn2)nc1]

The same procedure for 001 was followed to give 42 mg of a white solid in 48% yield. m/z ESI expected: 418.52, observed: 419.35. $^1$H NMR (500 MHz DMSO) δ 10.43 (br, 1H), 8.86 (d, J=2 Hz, 1H), 8.49 (s, 1H), 8.20-8.09 (m, 3H), 7.92-7.83 (m, 2H), 7.77-7.73 (m, 1H), 6.92 (s, 1H), 4.79 (d, J=5 Hz, 4H), 3.57-3.46 (m, 2H), 3.00 (m, 3H), 2.39 (s, 3H), 2.30-2.22 (m, 2H), 2.03-1.92, (m, 2H).

N-(3-(1-isopropylpiperidin-4-yl)-1-(5-methylpyridin-2-yl)-1H-pyrazol-5-yl)picolinamide (009)

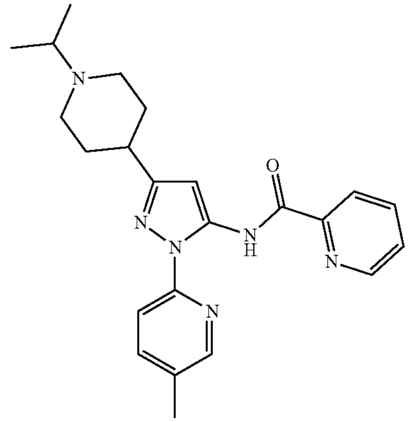 [SMILES: Cc1ccc(-n2nc(C3CCN(C(C)C)CC3)cc2NC(=O)c2ccccn2)nc1]

The same procedure for 001 was followed to give 42 mg of a white solid in 48% yield. m/z ESI expected: 404.52, observed: 405.68. $^1$H NMR (500 MHz DMSO) δ 9.03 (br, 1H), 8.85 (d, J=2 Hz, 1H), 8.49 (s, 1H), 8.22-8.09 (m, 2H), 7.92-7.51 (m, 2H), 7.77-7.73 (m, 1H), 6.92 (s, 1H), 3.57-3.46 (m, 2H), 3.19-3.09 (m, 2H), 3.04 (sept, J=5 Hz, 1H), 2.39 (s, 3H), 2.30-2.22 (m, 2H), 2.03-1.92, (m, 2H), 1.30 (d, J=7 Hz, 6H).

N-(3-(1-isopropylpiperidin-4-yl)-1-(pyridin-2-yl)-1H-pyrazol-5-yl)picolinamide (010)

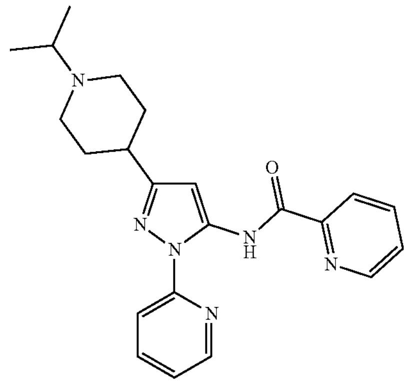 [SMILES: CC(C)N1CCC(c2cc(NC(=O)c3ccccn3)n(-c3ccccn3)n2)CC1]

The same procedure for 001 was followed to give 36 mg of a white solid in 41% yield. m/z ESI expected: 390.49, observed: 391.53. $^1$H NMR (500 MHz DMSO) δ 8.85 (d, J=2 Hz, 1H), 8.65 (d, J=2 Hz, 1H), 8.22-8.05 (m, 3H), 7.95 (d, J=5 Hz, 1H), 7.76-7.72 (m, 1H), 7.44-7.40 (m, 1H), 6.93 (s, 1H), 3.57-3.46 (m, 4H), 3.19-3.09 (m, 2H), 3.04 (sept, J=5 Hz, 1H), 2.30-2.22 (m, 2H), 2.03-1.92, (m, 2H), 1.30 (d, J=7 Hz, 6H).

N-(3-(1-methylpiperidin-4-yl)-1-(5-methylpyridin-2-yl)-1H-pyrazol-5-yl)picolinamide (011)

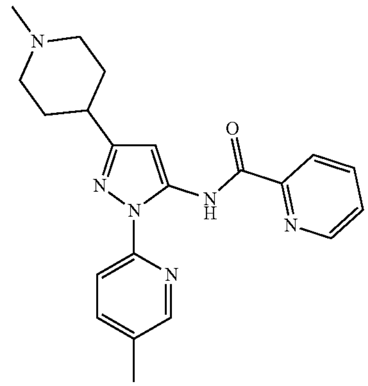 [SMILES: Cc1ccc(-n2nc(C3CCN(C)CC3)cc2NC(=O)c2ccccn2)nc1]

The same procedure for 001 was followed to give 39 mg of a white solid in 48% yield. m/z ESI expected: 376.46, observed: 377.62

N-(3-(1-isopropylpiperidin-4-yl)-1-(5-methylpyridin-2-yl)-1H-pyrazol-5-yl)-6-(1H-pyrazol-5-yl)picolinamide (012)
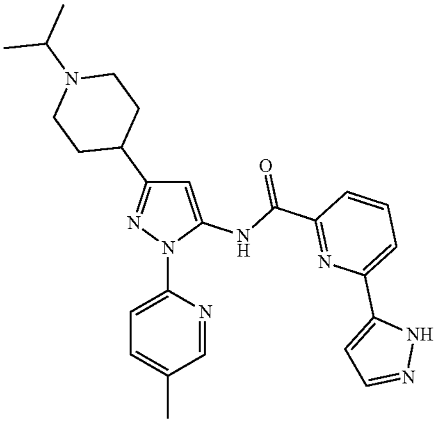 [SMILES: Cc1ccc(-n2nc(C3CCN(C(C)C)CC3)cc2NC(=O)c2cccc(-c3ccn[nH]3)n2)nc1]
The same procedure for 001 was followed to give 33 mg of a white solid in 34% yield. m/z ESI expected: 470.58, observed: 471.37
Example 2: Preparation of Compounds 013 to 016
Scheme 2.
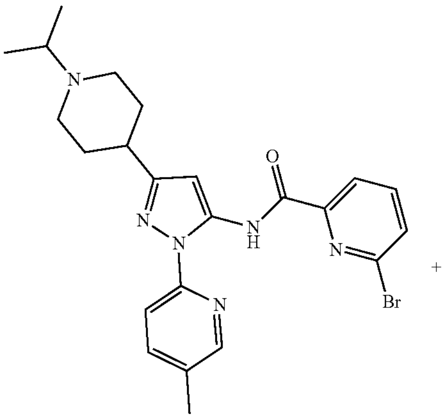
4
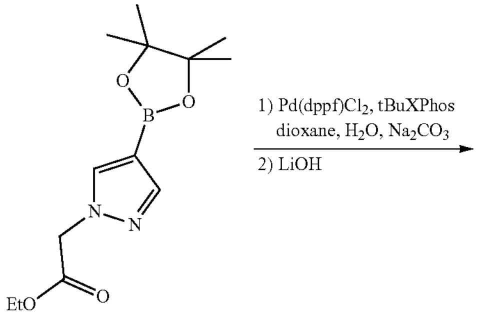
5
-continued
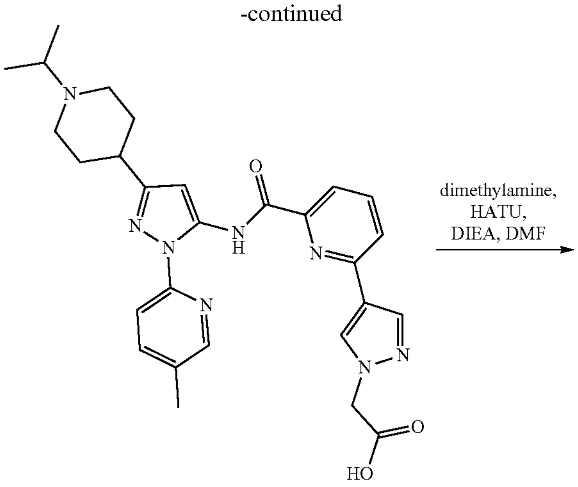
6
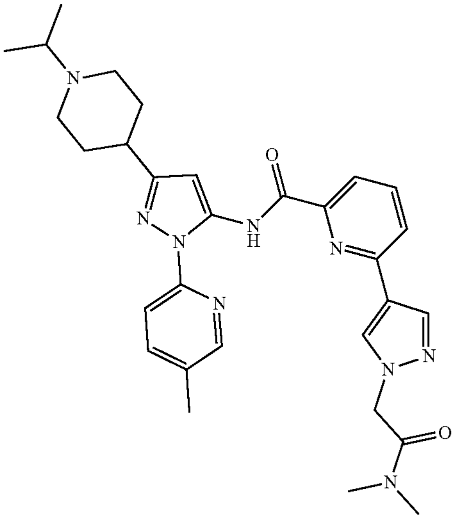
013
2-(4-(6-((3-(1-isopropylpiperidin-4-yl)-1-(5-methylpyridin-2-yl)-1H-pyrazol-5-yl)carbamoyl)pyridin-2-yl)-1H-pyrazol-1-yl)acetic acid (6)
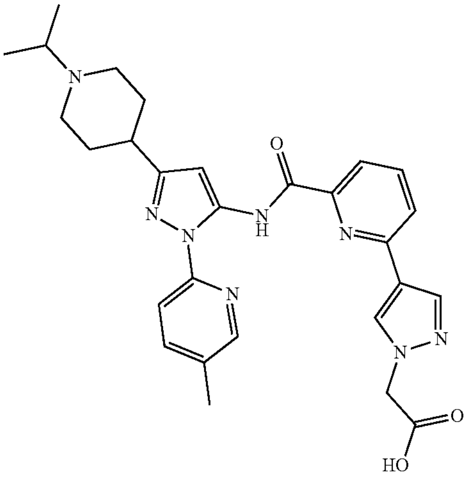 [SMILES: Cc1ccc(-n2nc(C3CCN(C(C)C)CC3)cc2NC(=O)c2cccc(-c3cnn(CC(=O)O)c3)n2)nc1]

To a solution of 6-bromo-N-(3-(1-isopropylpiperidin-4-yl)-1-(5-methylpyridin-2-yl)-1H-pyrazol-5-yl)picolinamide (4, 40 mg, 0.083 mmol, prepared using the same procedure as 3) dissolved in 1,4-dioxane (5 mL) was added ethyl 2-(4-(4,4,5,5-tetramethyl-1,3,2-dioxaborolan-2-yl)-1H-pyrazol-1-yl)acetate (5, 27 mg, 0.091 mmol) followed by $Na_2CO_3$ (2M aqueous solution, 0.21 mL, 0.415 mmol). The mixture was degassed in a sonicator for 2 minutes. Pd(dppf)$Cl_2$ (7 mg, 0.01 mmol) and t-BuXPhos (6 mg, 0.015 mmol) were added and the mixture heated to 90° C. in a sealed vial for 1 hour. The reaction mixture was cooled to room temperature, and LiOH monohydrate (17 mg, 0.415 mmol) was added. The reaction mixture was stirred at room temperature for 2 hours, filtered, and purified by reversed phase HPLC to give the desired compound as a beige solid (16 mg, 40% yield). m/z expected: 528.26, observed: 529.61.

6-(1-(2-(dimethylamino)-2-oxoethyl)-1H-pyrazol-4-yl)-N-(3-(1-isopropylpiperidin-4-yl)-1-(5-methylpyridin-2-yl)-1H-pyrazol-5-yl)picolinamide (013)

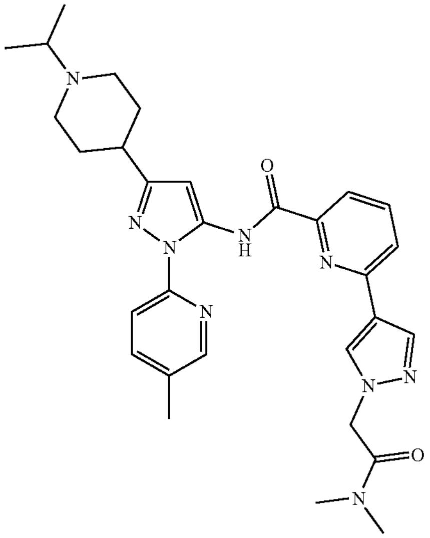 [SMILES: Cc1ccc(-n2nc(C3CCN(C(C)C)CC3)cc2NC(=O)c2cccc(-c3cnn(CC(=O)N(C)C)c3)n2)nc1]

To a solution of 2-(4-(6-((3-(1-isopropylpiperidin-4-yl)-1-(5-methylpyridin-2-yl)-1H-pyrazol-5-yl)carbamoyl)pyridin-2-yl)-1H-pyrazol-1-yl)acetic acid (6, 20 mg, 0.038 mmol) in DMF (2 mL) was added dimethylamine (2M in THF, 23 μL, 0.046 mmol) followed by HATU (29 mg, 0.076 mmol). DIEA (33 μL, 0.19 mmol) was added, and the mixture stirred for 20 min at room temperature, filtered, and purified by reversed phase HPLC to give the desired compound as a yellow solid (16 mg, 76% yield). m/z expected: 555.69, observed: 556.34.

N-(3-(1-isopropylpiperidin-4-yl)-1-(5-methylpyridin-2-yl)-1H-pyrazol-5-yl)-6-(1-(2-(methylamino)-2-oxoethyl)-1H-pyrazol-4-yl)picolinamide (014)

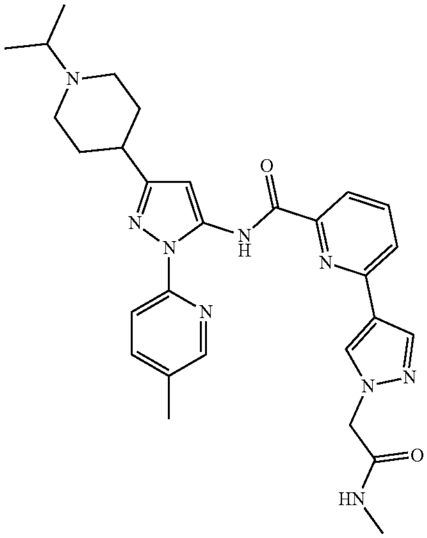 [SMILES: CNC(=O)Cn1cc(-c2cccc(C(=O)Nc3cc(C4CCN(C(C)C)CC4)nn3-c3ccc(C)cn3)n2)cn1]

The same procedure for 013 was followed to give 20 mg of the product in 95% yield. m/z expected: 541.66, observed: 542.82; $^1$H NMR (500 MHz DMSO) δ 9.03 (s, 1H), 8.46 (s, 2H), 8.23 (s, 1H), 8.10-7.98 (m, 3H), 7.93-7.99 (m, 2H), 6.98 (s, 1H), 4.96 (s, 2H), 3.57-3.47 (m 4H), 3.20-3.10 (m, 2H), 3.04 (sept, J=5 Hz, 1H), 2.68 (d, 3H), 2.36 (s, 3H), 2.30-2.22 (m, 2H), 2.01-1.91 (m, 2H), 1.30 (d, J=7 Hz, 6H).

6-(1-(2-amino-2-oxoethyl)-1H-pyrazol-4-yl)-N-(3-(1-isopropylpiperidin-4-yl)-1-(5-methylpyridin-2-yl)-1H-pyrazol-5-yl)picolinamide (015)

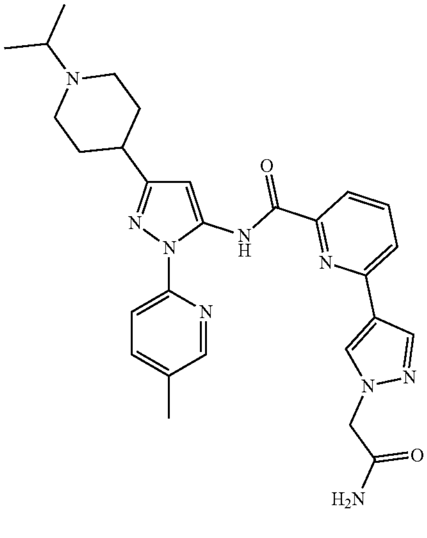 [SMILES: Cc1ccc(-n2nc(C3CCN(C(C)C)CC3)cc2NC(=O)c2cccc(-c3cnn(CC(N)=O)c3)n2)nc1]

The same procedure for 013 was followed to give 12 mg of the product in 60% yield. m/z expected: 527.63, observed: 528.49; $^1$H NMR (500 MHz DMSO) δ 9.02 (s, 1H), 8.44 (s, 2H), 8.23 (s, 1H), 8.10-7.98 (m, 3H), 7.95-7.90 (m, 2H), 7.71 (s, 1H), 7.38 (s, 1H), 6.98 (s, 1H), 4.97 (s, 2H), 3.57-3.47 (m 3H), 3.20-3.10 (m, 2H), 3.04 (sept, J=5 Hz, 1H), 2.37 (s, 3H), 2.30-2.22 (m, 2H), 2.01-1.91 (m, 2H), 1.30 (d, J=7 Hz, 6H).

6-(1-(2-amino-2-oxoethyl)-1H-pyrazol-4-yl)-N-(3-(1-isopropylpiperidin-4-yl)-1-(pyridin-2-yl)-1H-pyrazol-5-yl)picolinamide (016)

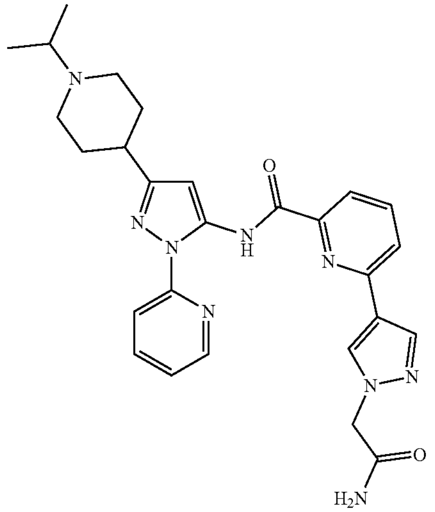 [SMILES: CC(C)N1CCC(c2cc(NC(=O)c3cccc(-c4cnn(CC(N)=O)c4)n3)n(-c3ccccn3)n2)CC1]

The same procedure for 013 was followed to give 57 mg of the product in 84% yield. m/z expected: 513.61, observed: 514.47; $^{1}$H NMR (500 MHz DMSO) δ 9.03 (s, 1H), 8.61 (d, J=2 Hz, 1H), 8.42 (s, 1H), 8.22 (s, 1H), 8.12-8.06 (m, 2H), 8.01-7.97 (m, 3H), 7.71 (s, 1H), 7.40 (m, 2H), 6.99 (s, 1H), 4.94 (s, 2H), 3.57-3.47 (m 4H), 3.20-3.08 (m, 3H), 3.04 (sept, J=5 Hz, 1H), 2.31-2.22 (m, 2H), 2.01-1.91 (m, 2H), 1.31 (d, J=7 Hz, 6H).

Example 3: Preparation of Compound 017

Scheme 3.

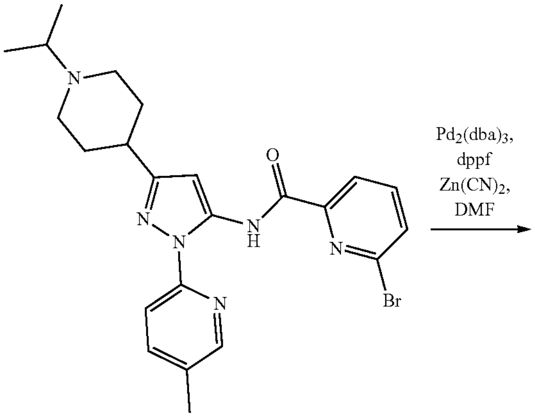

4

-continued

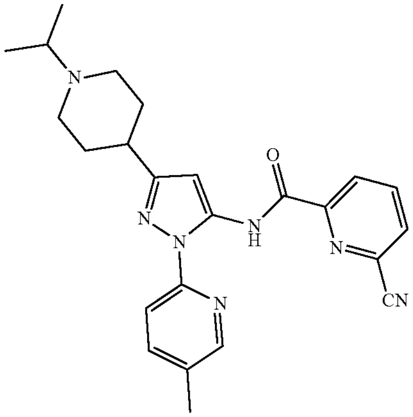

017

6-cyano-N-(3-(1-isopropylpiperidin-4-yl)-1-(5-methylpyridin-2-yl)-1H-pyrazol-5-yl)picolinamide (017)

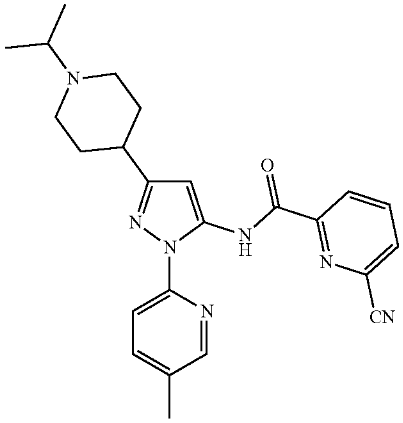 [SMILES: Cc1ccc(-n2nc(C3CCN(C(C)C)CC3)cc2NC(=O)c2cccc(C#N)n2)nc1]

6-bromo-N-(3-(1-isopropylpiperidin-4-yl)-1-(5-methylpyridin-2-yl)-1H-pyrazol-5-yl)picolinamide (4, 50 mg, 0.103 mmol, prepared using the same procedure as 3) was dissolved in DMF (2 mL), and the mixture was degassed using sonication for 1 minute. $Pd_2(dba)_3$ (10 mg, 0.01 mmol), dppf (12 mg, 0.02 mmol), and $Zn(CN)_2$ (26 mg, 0.210 mmol) were added, and the mixture was stirred at 120° C. for 2 hr. The mixture was filtered and purified by reverse phase HPLC using a gradient of 1-70% ACN in $H_2O$ to give the desired product as a brown oil (3 mg, 7% yield). m/z expected: 429.53, observed: 430.71; $^{1}$H NMR (500 MHz DMSO) δ 9.15 (s, 1H), 8.42 (dd, J=6.9 Hz, 2.1 Hz, 1H), 8.37-8.33 (m, 2H), 8.31 (s, 1H), 7.92 (dd, J=8.0 Hz, 1.8 Hz, 1H), 7.84 (d, J=8.5 Hz, 1H), 6.85 (s, 1H), 3.16-3.10 (m, 5H), 3.05-3.00 (m, 1H), 2.37 (s, 3H), 2.26-2.23 (m, 2H), 1.99-1.90 (m, 2H), 1.29 (d, J=6.6 Hz, 6H).

Example 4: Preparation of Compounds 018 and 019

Scheme 4.

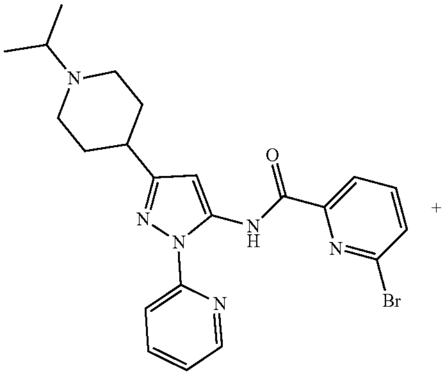

7

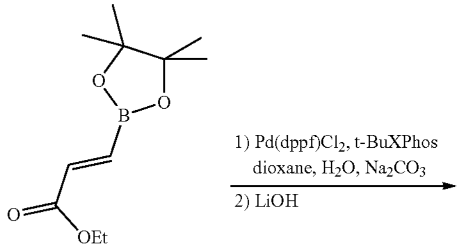

8

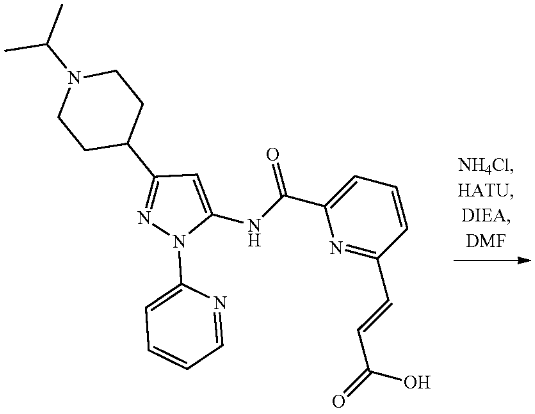

9

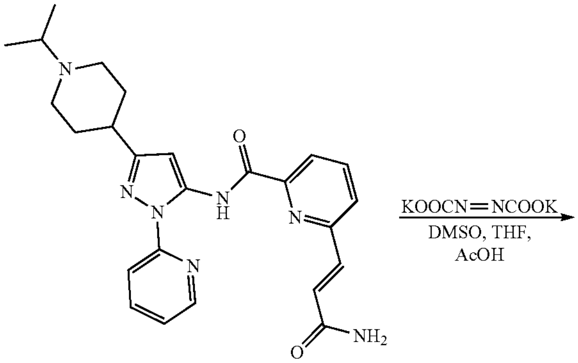

018

-continued

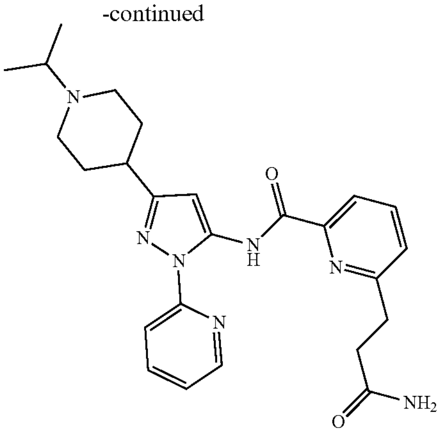

018

(E)-3-(6-((3-(1-isopropylpiperidin-4-yl)-1-(pyridin-2-yl)-1H-pyrazol-5-yl)carbamoyl)pyridin-2-yl)acrylic acid (9)

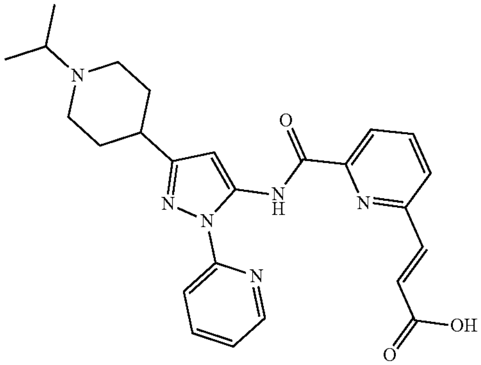 [SMILES: CC(C)N1CCC(c2cc(NC(=O)c3cccc(/C=C/C(=O)O)n3)n(-c3ccccn3)n2)CC1]

The same procedure for 6 was followed to give the product in 99% yield. m/z expected: 460.54, observed: 461.55.

(E)-6-(3-amino-3-oxoprop-1-en-1-yl)-N-(3-(1-isopropylpiperidin-4-yl)-1-(pyridin-2-yl)-1H-pyrazol-5-yl)picolinamide (018)

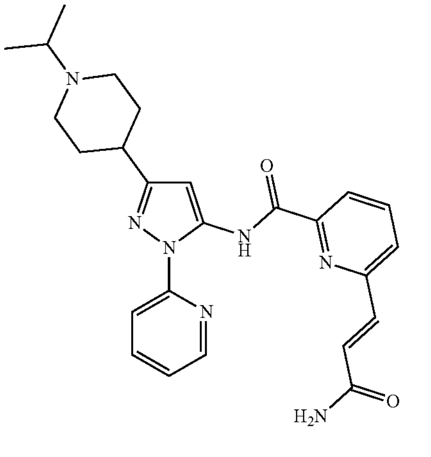 [SMILES: CC(C)N1CCC(c2cc(NC(=O)c3cccc(/C=C/C(N)=O)n3)n(-c3ccccn3)n2)CC1]

The same procedure for 013 was followed, substituting dimethylamine with ammonium chloride, to give the product in 24% yield. m/z expected: 459.55, observed: 460.50.

$^1$H NMR (500 MHz DMSO) δ 9.08 (br, 1H), 8.59 (d, J=2 Hz, 1H), 8.18-8.14 (m, 3H), 8.01, (d, J=9 Hz, 1H), 7.94 (m, 1H), 7.84 (br, 1H), 7.64 (d, J=10 Hz, 1H), 7.43 (m, 1H), 7.35 (br, 1H), 7.18 (d, J=10 Hz, 1H), 6.97 (s, 1H), 3.57-3.47 (m 3H), 3.20-3.10 (m, 2H), 3.04 (sept, J=5 Hz, 1H), 2.30-2.22 (m, 2H), 2.03-1.92, (m, 2H), 1.31 (d, J=7 Hz, 6H).

6-(3-amino-3-oxopropyl)-N-(3-(1-isopropylpiperidin-4-yl)-1-(pyridin-2-yl)-1H-pyrazol-5-yl)picolinamide (019)

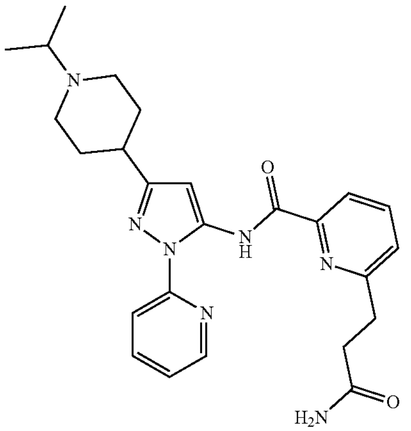 [SMILES: CC(C)N1CCC(c2cc(NC(=O)c3cccc(CCC(N)=O)n3)n(-c3ccccn3)n2)CC1]

To a solution of (E)-6-(3-amino-3-oxoprop-1-en-1-yl)-N-(3-(1-isopropylpiperidin-4-yl)-1-(pyridin-2-yl)-1H-pyrazol-5-yl)picolinamide (018, 6 mg, 0.013 mmol) in THF:DMSO 1:1 (3 mL) was added dipotassium azodicarboxylate (51 mg, 0.261 mmol) and acetic acid (30 μL) portion wise over 1 hr. The mixture was warmed to room temperature and stirred overnight. The reaction was quenched with $H_2O$, extracted with EtOAc, dried over $MgSO_4$ and condensed to give a yellow oil that was purified by reverse phase HPLC to give the desired product as a yellow solid 2 mg, 33% yield. m/z expected: 461.46, observed: 462.46. $^1$H NMR (500 MHz DMSO) δ 9.06 (br, 1H), 8.66 (d, J=2 Hz, 1H), 8.12-7.96 (m, 4H), 7.61 (m, 1H), 7.41 (m, 2H), 6.92 (s, 1H), 3.57-3.47 (m 3H), 3.18-3.10 (m, 5H), 3.04 (sept, J=5 Hz, 1H), 2.66 (t, J=5 Hz, 2H), 2.30-2.22 (m, 2H), 2.03-1.92, (m, 2H), 1.31 (d, J=7 Hz, 6H).

Example 5: Preparation of Compound 020

Scheme 5.

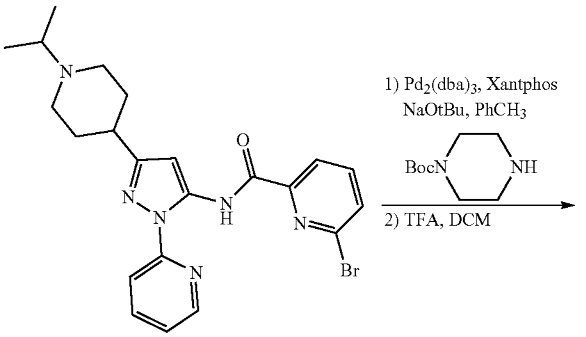

7

-continued

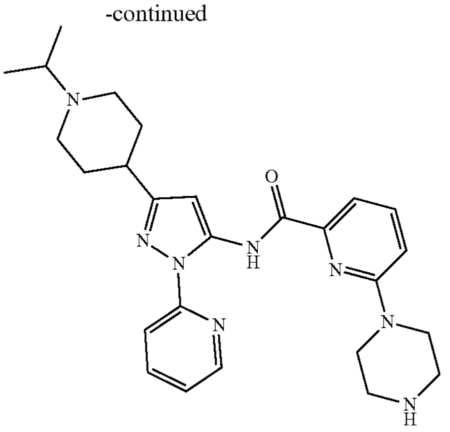

020

N-(3-(1-isopropylpiperidin-4-yl)-1-(pyridin-2-yl)-1H-pyrazol-5-yl)-6-(piperazin-1-yl)picolinamide (020)

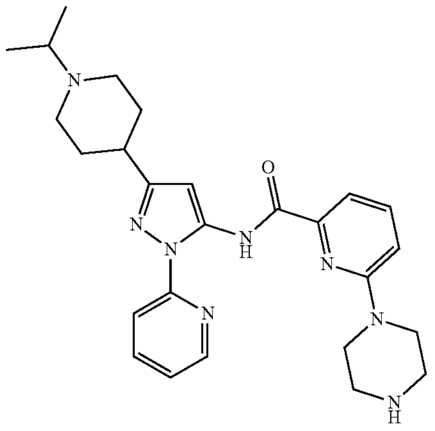 [SMILES: CC(C)N1CCC(c2cc(NC(=O)c3cccc(N4CCNCC4)n3)n(-c3ccccn3)n2)CC1]

6-bromo-N-(3-(1-isopropylpiperidin-4-yl)-1-(pyridin-2-yl)-1H-pyrazol-5-yl)picolinamide (7, 50 mg, 0.106 mmol, prepared using the same procedure as 3), tert-butyl piperazine-1-carboxylate (24 mg, 0.128 mmol) and NaOtBu (31 mg, 0.318 mmol) were dissolved in toluene (3 mL), and the mixture was degassed using sonication for 1 minute. $Pd_2(dba)_2$ (6 mg, 0.006 mmol) and Xantphos (6 mg, 0.009 mmol) were added, and the mixture was stirred at 100° C. for 2 hours under nitrogen. The reaction was quenched with $H_2O$, extracted with EtOAc, dried over $MgSO_4$ and condensed to give a brown oil that was dissolved in DCM (10 mL). TFA (1 mL) was added, and the mixture was stirred for 30 minutes. The solvent was removed and the crude material purified by reverse phase HPLC using a gradient of 1-70% ACN in $H_2O$ to give 5 mg (10% yield) of the desired product as a white solid. m/z expected: 474.61, observed: 475.62. $^1$H NMR (500 MHz DMSO) δ 9.04 (s, 1H), 8.38 (d, J=5 Hz, 1H), 8.13-7.99 (m, 2H), 7.92 (t, J=8.0 Hz, 1H), 7.58 (d, J=7 Hz, 1H), 7.43 (m, 1H), 7.30 (d, J=7 Hz, 1H), 6.98 (s, 1H), 3.93 (m, 4H), 3.57-3.47 (m 4H), 3.36-3.32 (m, 4H), 3.18-3.09 (m, 2H), 3.04 (sept, J=5 Hz, 1H), 2.26-2.23 (m, 2H), 1.99-1.90 (m, 2H), 1.29 (d, J=6.6 Hz, 6H).

Example 6: IRAK1 and IRAK4 Enzymatic Assays

To measure the $IC_{50}$ values of compounds herein against IRAK4, a Z'-LYTE assay (ThermoFisher) was used. Briefly, 2.5 μL of different concentrations of the compounds in 1% DMSO were added to 2.4 μL kinase buffer (50 mM HEPES pH 7.5, 0.01% BRIJ-35, 10 mM $MgCl_2$, 1 mM EGTA) in each well of a 384-well plate (Corning Cat. #3676). 5 μL of 2× IRAK4/Ser/Thr 07 mixture (prepared in 50 mM HEPES pH 7.5, 0.01% BRIJ-35, 10 mM $MnCl_2$, 2 mM DTT, and 0.02% $NaN_3$) and 2.5 μL of 4× ATP solution (4× ATP, 50 mM HEPES, pH 7.5, 0.01% BRIJ-35, 10 mM $MgCl_2$, 1 mM EGTA) were added to each well. The plate was shaken for 30 seconds, and then incubated at room temperature for 60 minutes. 5 μL of a 1:100000 dilution of Development Reagent A was added to each well. The plate was shaken for 30 seconds and incubated for 60 minutes at room temperature. The plate was subsequently read on a fluorescence plate reader, and the emissions ratio was calculated to determine the ratio of Ser/Thr 07 phosphorylated by the reaction. Emissions Ratio=Coumarin Emission (443 nm)/Flourescein Emission (520 nm).

To measure the $IC_{50}$ values of the compounds herein against IRAK1, the Adapta Universal Kinase Assay (ThermoFisher) was used. Briefly, 100 nL of different concentrations of the compounds in 100% DMSO were added to each well of a 384-well plate (Corning Cat. #4512). 2.4 μL of 30 mM HEPES, 2.5 μL of 4× ATP solution (in water), and 5 μL of 2× IRAK1/Histone H3 (1-20) peptide mixture (prepared in 50 mM HEPES pH 7.5, 0.01% BRIJ-35, 10 mM $MgCl_2$, 1 mM EGTA) were added to each well. The plate was shaken for 30 seconds and centrifuged for 1 minute at 1000×g. The plate was then incubated at room temperature for 60 minutes. 5 μL of Detection Mix was added to each well. The plate was shaken for 30 seconds and centrifuged for 1 minute at 1000×g. The plate was then incubated at room temperature for 60 minutes. The plate was subsequently read on a fluorescence plate reader, and the emissions ratio was calculated to determine the ratio of ATP to ADP. Emissions Ratio=AF647 Emission (665 nm)/Europium Emission (615 nm).

The data obtained from these assays are shown in Table 2 below.

TABLE 2

IRAK1 and IRAK4 inhibitory activity of IRAK4 inhibitors

| Compound No. | IRAK1 $IC_{50}$ (nM) | IRAK4 $IC_{50}$ (nM) |
|---|---|---|
| 001 | 8 | 4 |
| 002 | 36 | 3 |
| 003 | 66 | 6 |
| 004 | 372 | 24 |
| 005 | 183 | 37 |
| 006 | 15 | 6 |
| 007 | 317 | 31 |
| 008 | 1350 | 148 |
| 009 | 1650 | 55 |
| 010 | 1100 | 43 |
| 011 | 835 | 170 |
| 012 | 7 | 3 |
| 013 | 718 | 45 |
| 014 | 656 | 36 |
| 015 | 450 | 9 |
| 016 | 828 | 39 |
| 017 | 90 | 9 |
| 018 | 234 | 24 |
| 019 | 242 | 47 |
| 020 | 10000 | 561 |

Example 7: Comparative Cellular Activity of IRAK4 Inhibitors

The CellTiter-Glo® Luminescent cell viability assay (Promega, Madison WI) was used to assess the dose-response of inhibitors alone or in combination. Cells were seeded into 384 well plates with the EL406 Combination Washer Dispenser (BioTek Instruments, Inc.) and inhibitors were injected into culture media with the JANUS Automated Workstation (PerkinElmer Inc., Waltham MA). Cells were incubated with inhibitors for 72 hours at 37° C. Luminescent measurements to assess cell viability were performed using the 2104 Envision® Multilabel Reader (PerkinElmer Inc.). Drug interactions were assessed by CalcuSyn 2.0 software (Biosoft, Cambridge UK) based on Chou TC.

compound 015

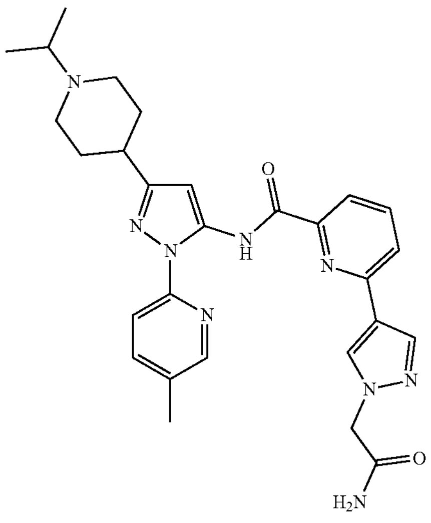

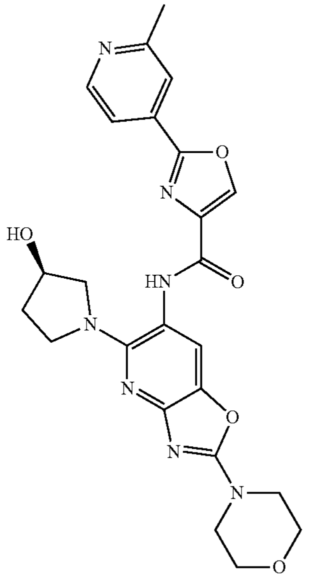

CA-4948

-continued

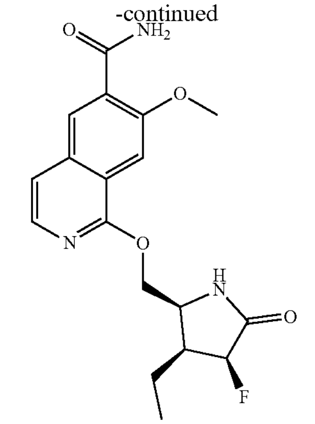

PF06650833

Cellular IRAK4 inhibitory activities of compound 015 and two commercial IRAK4 inhibitors, CA-4948 and PF06650833, were screened across multiple cell lines. Compound 015 was shown to be more potent in most cell lines than either CA-4948 or PF06650833.

TABLE 3

$ED_{50}$ values of select IRAK4 inhibitors in various cell lines

| Cell Line | $ED_{50}$ (M) compound 015 | $ED_{50}$ (M) CA-4948 | $ED_{50}$ (M) PF06650833 |
|---|---|---|---|
| BCWM.1 | $3.33 \times 10^{-6}$ | $1.99 \times 10^{-6}$ | $1.10 \times 10^{-5}$ |
| MWCL-1 | $6.92 \times 10^{-6}$ | $1.19 \times 10^{-5}$ | $1.83 \times 10^{-5}$ |
| TMD8 | $3.92 \times 10^{-6}$ | $9.37 \times 10^{-6}$ | $2.41 \times 10^{-5}$ |
| HBL-1 | $2.20 \times 10^{-6}$ | $1.11 \times 10^{-5}$ | $1.48 \times 10^{-5}$ |
| OCI-Ly7 | $3.11 \times 10^{-6}$ | $1.30 \times 10^{-5}$ | $9.80 \times 10^{-6}$ |
| OCI-Ly19 | $1.22 \times 10^{-6}$ | $2.20 \times 10^{-6}$ | $5.87 \times 10^{-6}$ |
| Ramos | $3.62 \times 10^{-7}$ | | $2.87 \times 10^{-5}$ |
| RPMI-8226 | $6.78 \times 10^{-6}$ | $1.40 \times 10^{-5}$ | $8.05 \times 10^{-5}$ |
| SU-DHL-6 | $1.72 \times 10^{-6}$ | $8.69 \times 10^{-6}$ | |
| JeKo-1 | $6.26 \times 10^{-6}$ | $6.57 \times 10^{-6}$ | |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

The invention claimed is:

1. A compound of Formula (Ia3):

(I-a3)

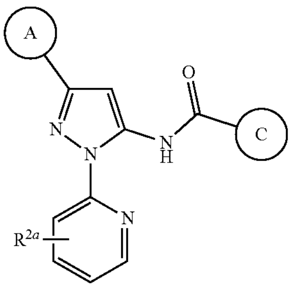

or a pharmaceutically acceptable salt thereof, wherein:

$R^{2a}$ is H, $C_{1-4}$ alkyl, cyclopropyl, cyclobutyl, —$CF_3$, —$CHF_2$, —$CH_2F$, $C_{1-4}$ alkoxy, halo, or —CN;

A is $C_{3-10}$ cycloalkyl or 4- to 10-membered heterocyclyl, wherein the cycloalkyl and heterocyclyl are unsubstituted or substituted with one, two, or three $R^1$;

$R^{A2}$ is H;

C is pyridinyl that is unsubstituted or substituted with one, two, or three $R^3$;

$R^1$, independently for each occurrence, is $C_{1-8}$ alkyl, $C_{1-8}$ haloalkyl, $C_{1-8}$ alkoxy, halo, $C_{3-8}$ cycloalkyl, or 3- to 8-membered heterocyclyl;

$R^3$, independently for each occurrence, is —OH, —CN, halo, —C(X)O$R^5$, —C(X)N($R^5$)($R^6$), $C_{1-8}$ alkyl, $C_{2-8}$ alkenyl, $C_{1-8}$ haloalkyl, $C_{1-8}$ alkoxy, $C_{3-10}$ cycloalkyl, 4- to 10-membered heterocyclyl, $C_{6-10}$ aryl, 5- to 10-membered heteroaryl, $C_{1-3}$ alkyl-(4- to 10-membered heterocyclyl), $C_{1-3}$ alkyl-(5- to 10-membered heteroaryl), —O—$C_{1-3}$ alkyl-(4- to 10-membered heterocyclyl), or —O—$C_{1-3}$ alkyl-(5- to 10-membered heteroaryl) wherein the alkyl, alkenyl, haloalkyl, alkoxy, cycloalkyl, heterocyclyl, aryl, heteroaryl, alkylheterocyclyl, alkylheteroaryl, —O-alkylheterocyclyl, and —O-alkylheteroaryl are unsubstituted or substituted with one, two, or three $R^4$;

$R^4$, independently for each occurrence, is oxo, —OH, —CN, halo, $C_{1-4}$ alkyl, $C_{1-4}$ haloalkyl, $C_{1-4}$ alkoxy, —$C_{0-3}$ alkyl-C(X)O$R^5$, —$C_{0-3}$ alkyl-C(X)N($R^5$)($R^6$), or —$C_{0-3}$ alkyl-(5- to 10-membered heteroaryl), wherein the alkylheteroaryl is unsubstituted or substituted with one, two, or three $C_{1-3}$ alkyl or halo;

X is, independently for each occurrence, O or S;

and $R^5$ and $R^6$ are each, independently, hydrogen or $C_{1-4}$ alkyl;

provided that when $R^{2a}$ is H, either $R^1$ is not isopropyl or $R^3$ is not

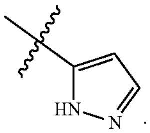 [SMILES: *c1ccn[nH]1]

.

2. The compound of claim 1, or a pharmaceutically acceptable salt thereof, wherein A is $C_{4-6}$ cycloalkyl or 4- to 6-membered heterocyclyl, wherein the cycloalkyl or heterocyclyl are unsubstituted or substituted with one, two, or three $R^1$.

3. The compound of claim 1, or a pharmaceutically acceptable salt thereof, wherein A is piperidinyl that is unsubstituted or substituted with one, two, or three $R^1$.

4. The compound of claim 1, or a pharmaceutically acceptable salt thereof, wherein A is substituted with one $R^1$.

5. The compound of claim 1, or a pharmaceutically acceptable salt thereof, wherein $R^1$, independently for each occurrence, is $C_{1-4}$ alkyl, $C_{1-4}$ haloalkyl, $C_{1-4}$ alkoxy, halo, $C_{3-6}$ cycloalkyl, or 3- to 6-membered heterocyclyl.

6. The compound of claim 1, or a pharmaceutically acceptable salt thereof, wherein A is selected from the group consisting of:

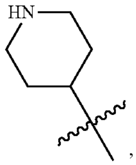 , 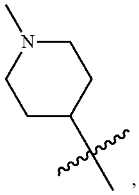 , 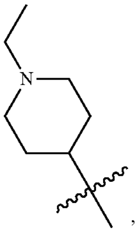 ,

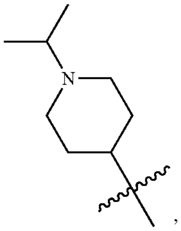 , 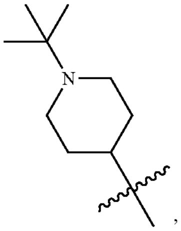 , 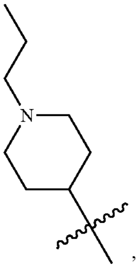 ,

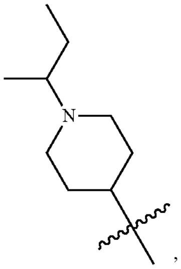 , 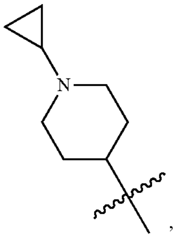 , 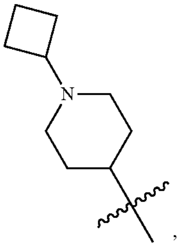 ,

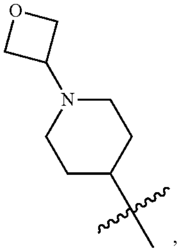 , 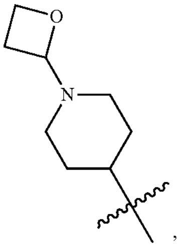 ,

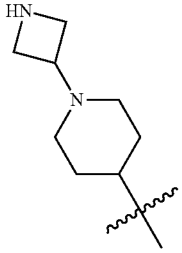 and 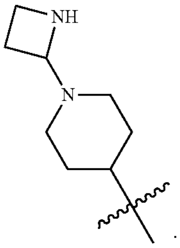 .

7. The compound of claim 1, or a pharmaceutically acceptable salt thereof, having a structure according to Formula (I-a4):

(1-a4)

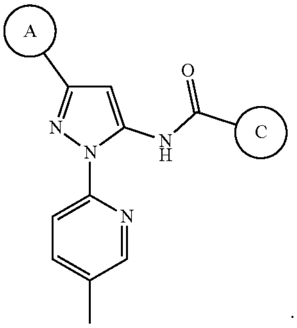

.

8. The compound of claim 1, or a pharmaceutically acceptable salt thereof, having a structure according to Formula (I-a5):

(1-a5)

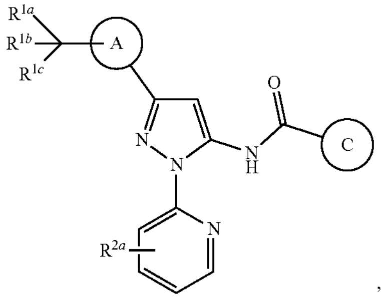

, wherein:

$R^{1a}$ is H or $CH_3$;

$R^{1b}$ is H or $C_{1-3}$ alkyl;

$R^{1c}$ is H or $C_{1-3}$ alkyl; or $R^{1a}$ is H and $R^{1b}$ and $R^{1c}$ taken together form a $C_{3-4}$ cycloalkyl or a 3- to 4-membered heterocyclyl along with the carbon atom to which they are attached; and $R^{2a}$ is H, $C_{1-4}$ alkyl, cyclopropyl, cyclobutyl, —$CF_3$, —$CHF_2$, —$CH_2F$, $C_{1-4}$ alkoxy, halo, or —CN.

9. The compound of claim 1, or a pharmaceutically acceptable salt thereof, wherein:

$R^3$, independently for each occurrence, is —C(X)N($R^5$)($R^6$), $C_{1-8}$ alkyl, $C_{2-8}$ alkenyl, $C_{3-10}$ cycloalkyl, 4- to 10-membered heterocyclyl, $C_{6-10}$ aryl, 5- to 10-membered heteroaryl, or $C_{1-3}$ alkyl-(5- to 10-membered heteroaryl) wherein the alkyl, alkenyl, cycloalkyl, heterocyclyl, aryl, heteroalkyl, and alkylheteroaryl are unsubstituted or substituted with one, two, or three $R^4$.

10. The compound of claim 1, or a pharmaceutically acceptable salt thereof, wherein C is represented by a formula selected from the group consisting of (II-a) to (II-1):

(II-a)

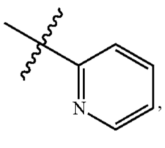

,

-continued (II-b)

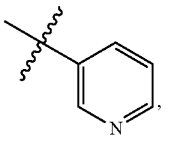

(II-c)

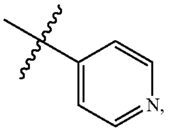

(II-d)

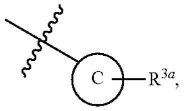

(II-e)

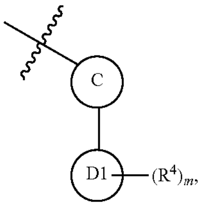

(II-f)

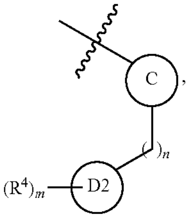

(II-g)

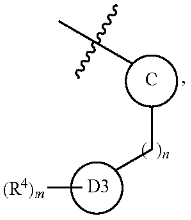

(II-h)

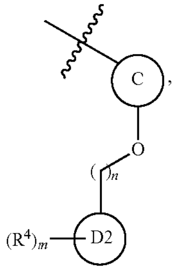

(II-i)

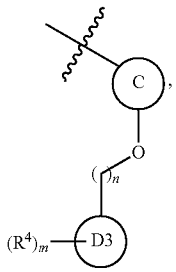

-continued (II-j)

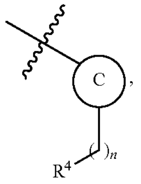

(II-k)

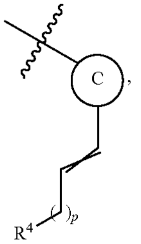

or (II-l)

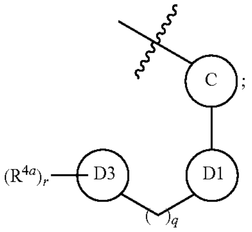

wherein:

$R^{3a}$ is —OH, —CN, halo, $C_{1-4}$ alkyl, $C_{1-4}$ haloalkyl, or $C_{1-4}$ alkoxy;

$R^{4a}$ is $C_{1-3}$ alkyl or halo;

D1 is $C_{3-10}$ cycloalkyl, 4- to 10-membered heterocyclyl, $C_{6-10}$ aryl, or 5- to 10-membered heteroaryl;

D2 is 4- to 10-membered heterocyclyl;

D3 is 5- to 10-membered heteroaryl;

m, p, q, and r are independently 0, 1, 2, or 3; and n is 1, 2, 3, or 4.

11. The compound of claim 10, or a pharmaceutically acceptable salt thereof, wherein:

D1 is 4- to 10-membered heterocyclyl, phenyl, or 5- to 6-membered heteroaryl; and D3 is 5- to 6-membered heteroaryl.

12. The compound of claim 10, or a pharmaceutically acceptable salt thereof, wherein:

D1 is tetrahydrofuryl, pyrrolidinyl, pyrrolidinonyl, tetrahydrothiophenyl, tetrahydropyranyl, tetrahydrothiopyranyl, piperidinyl, morpholinyl, piperazinyl, diazaspirodecanonyl, phenyl, pyrrolyl, furanyl, thiophenyl, pyrazolyl, imadazolyl, triazolyl, oxazolyl, isoxazolyl, thiazolyl, isothiazolyl, oxadiazolyl, pyridinyl, pyridazinyl, pyrimidinyl, or pyrazinyl;

D2 is tetrahydrofuryl, pyrrolidinyl, pyrrolidinonyl, tetrahydrothiophenyl, tetrahydropyranyl, tetrahydrothiopyranyl, piperidinyl, morpholinyl, piperazinyl, or diazaspirodecanonyl; and D3 is pyrrolyl, furanyl, thiophenyl, pyrazolyl, imadazolyl, triazolyl, oxazolyl, isoxazolyl, thiazolyl, isothiazolyl, oxadiazolyl, pyridinyl, pyridazinyl, pyrimidinyl, or pyrazinyl.

13. The compound of claim 1, or a pharmaceutically acceptable salt thereof, wherein:

$R^4$ is oxo, halo, $C_{1-4}$ alkyl, —$C_{0-3}$ alkyl-C(X)N($R^5$)($R^6$), or —$C_{0-3}$ alkyl-(5- to 10-membered heteroaryl), wherein the alkylheteroaryl is unsubstituted or substituted with one, two, or three $C_{1-3}$ alkyl or halo;
X is O; and
$R^5$ and $R^6$ are each, independently, hydrogen or methyl.
14. The compound of claim 1, selected from the group consisting of:
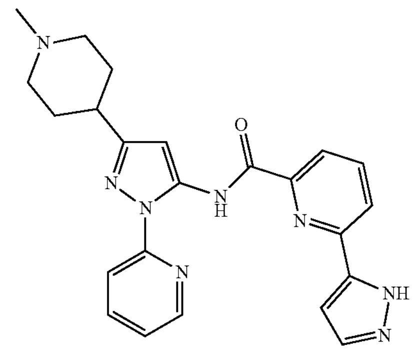
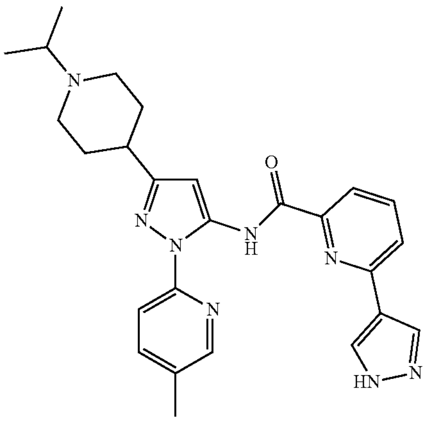
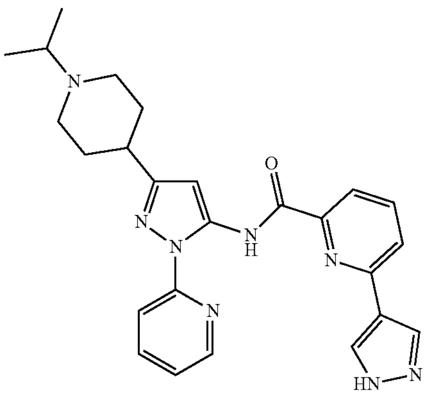
-continued
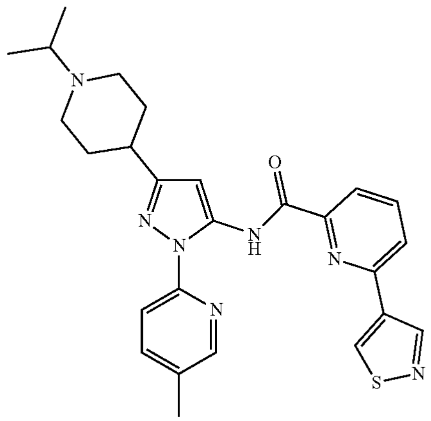
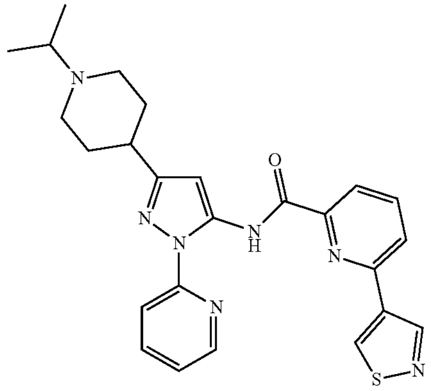
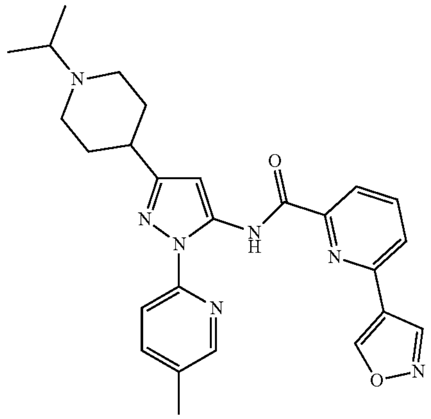
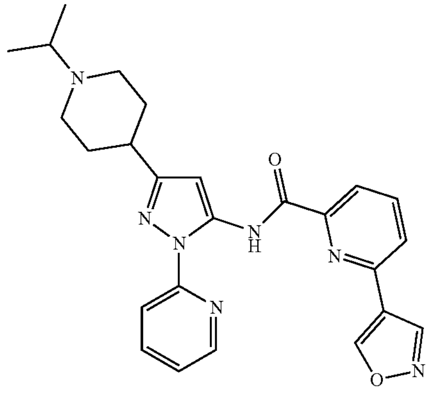

-continued
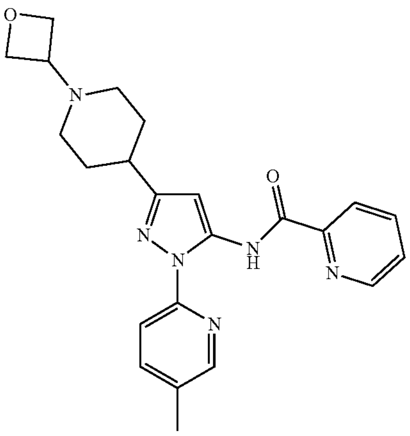
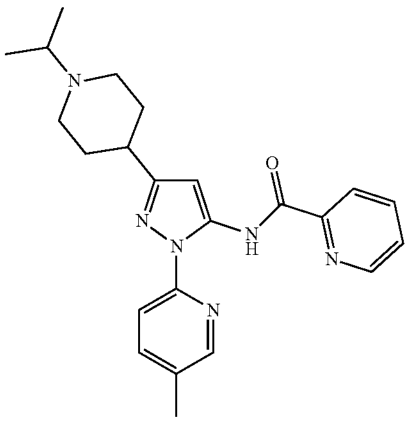
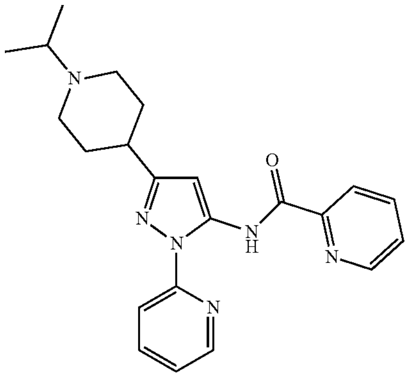
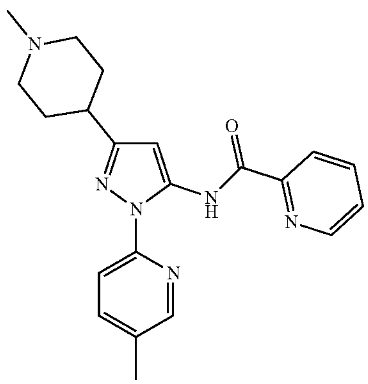
-continued
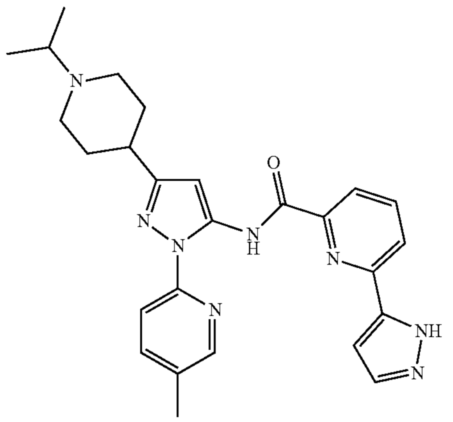
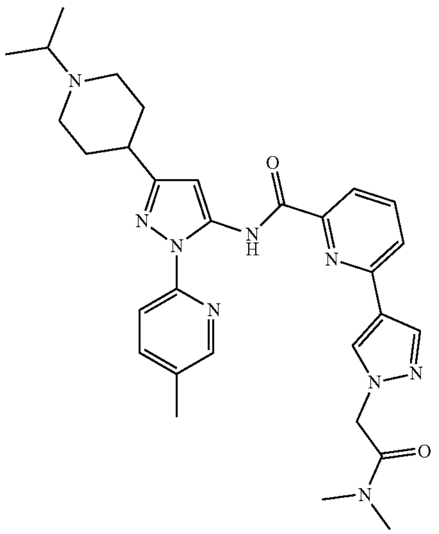
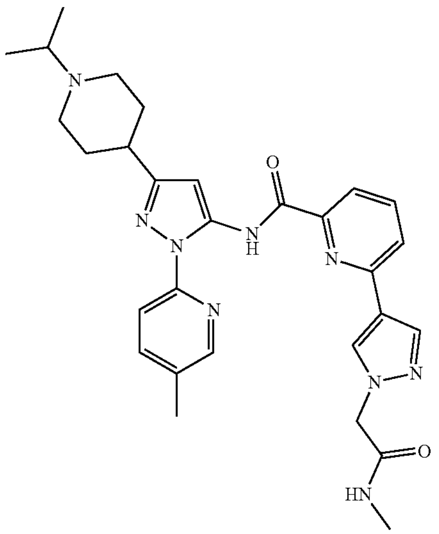

-continued

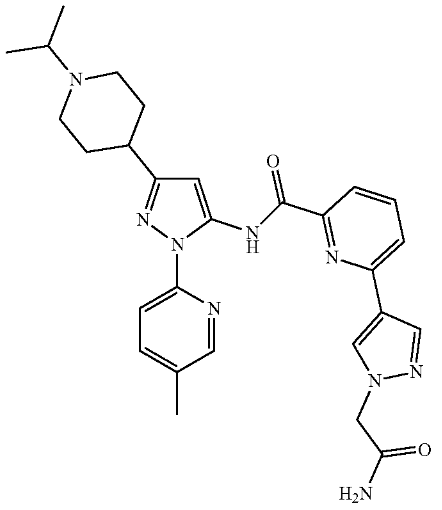

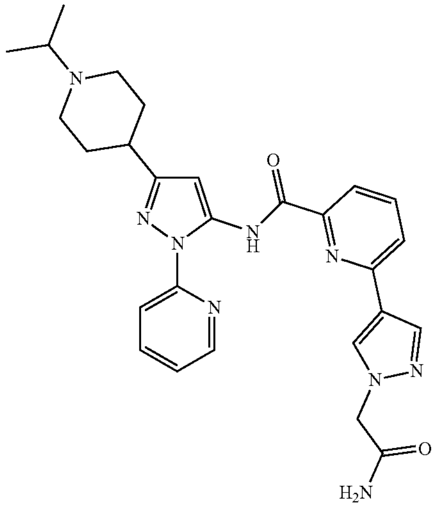

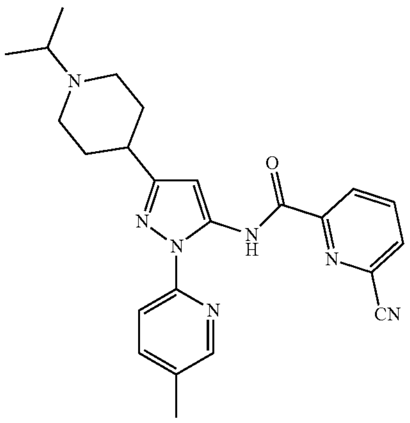

-continued

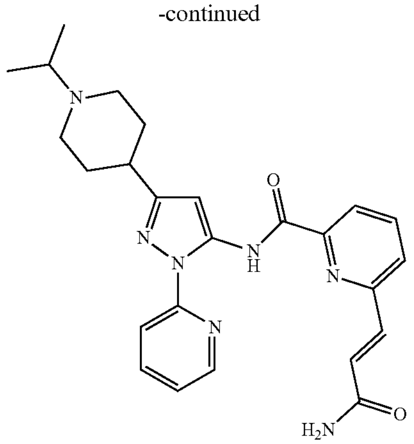

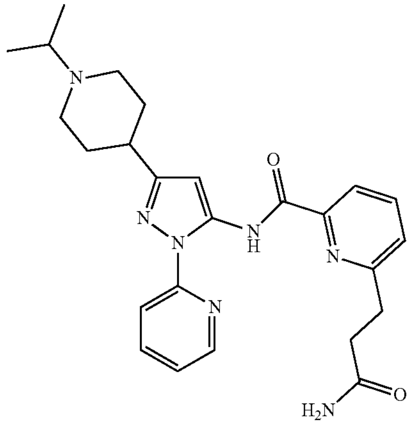

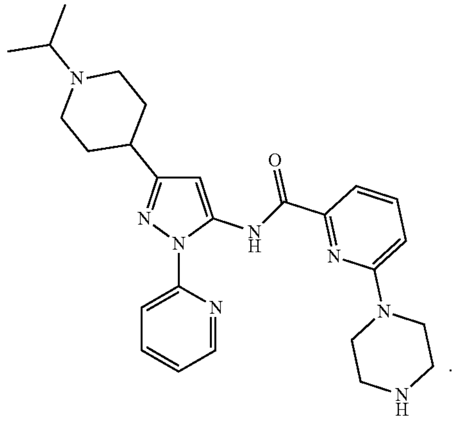

15. A pharmaceutical composition comprising a compound of claim 1, or a pharmaceutically acceptable salt thereof, and a pharmaceutically acceptable carrier.

16. A method of inhibiting interleukin-1 receptor-associated kinase 4 (IRAK4) in a subject in need thereof, the method comprising administering to the subject a therapeutically effective amount of a compound of claim 1, or a pharmaceutically acceptable salt thereof.

17. A method of treating a proliferative disease or disorder in a subject in need thereof comprising administering to the subject a therapeutically effective amount of a compound of any one of claim 1, or a pharmaceutically acceptable salt thereof.

18. A method of treating an inflammatory disease or disorder in a subject in need thereof comprising administering to the subject a therapeutically effective amount of a compound of claim 1, or a pharmaceutically acceptable salt thereof.

* * * * *